(12) United States Patent
Detweiler et al.

(10) Patent No.: US 11,707,308 B2
(45) Date of Patent: Jul. 25, 2023

(54) IMPLANT POSITIONER AND STERNAL PLATING SYSTEM

(71) Applicant: Jace Medical, LLC, Warsaw, IN (US)

(72) Inventors: Jason F. Detweiler, Warsaw, IN (US); Scott Steffensmeier, Winona Lake, IN (US)

(73) Assignee: Jace Medical, LLC, Warsaw, IN (US)

( * ) Notice: Subject to any disclaimer, the term of this patent is extended or adjusted under 35 U.S.C. 154(b) by 0 days.

(21) Appl. No.: 17/869,563

(22) Filed: Jul. 20, 2022

(65) Prior Publication Data

US 2022/0354551 A1 Nov. 10, 2022

Related U.S. Application Data

(63) Continuation of application No. 16/927,259, filed on Jul. 13, 2020, now Pat. No. 11,439,447, which is a continuation of application No. PCT/US2019/013805, filed on Jan. 16, 2019.

(60) Provisional application No. 62/619,261, filed on Jan. 19, 2018.

(51) Int. Cl.
*A61B 17/80* (2006.01)
*A61B 17/17* (2006.01)

(52) U.S. Cl.
CPC ........ *A61B 17/808* (2013.01); *A61B 17/1728* (2013.01); *A61B 17/8038* (2013.01); *A61B 17/8076* (2013.01); *A61B 17/1789* (2016.11)

(58) Field of Classification Search
CPC . A61B 17/1728; A61B 17/1789; A61B 17/80; A61B 17/8076; A61B 17/808; A61B 17/8872; A61B 17/90
See application file for complete search history.

(56) References Cited

U.S. PATENT DOCUMENTS

| | | | |
|---|---|---|---|
| 4,263,904 A | 4/1981 | Judet | |
| 7,189,237 B2 | 3/2007 | Huebner | |
| 7,909,848 B2* | 3/2011 | Patel | A61B 17/1757 606/280 |
| 7,935,123 B2* | 5/2011 | Fanger | A61B 17/1728 606/86 B |
| 8,414,594 B2 | 4/2013 | Berger et al. | |
| 8,523,862 B2 | 9/2013 | Murashko, Jr. | |
| 8,721,648 B2 | 5/2014 | Meridew | |

(Continued)

FOREIGN PATENT DOCUMENTS

| CA | 3088923 A1 | 7/2019 |
|---|---|---|
| EP | 3740146 A1 | 11/2020 |

(Continued)

OTHER PUBLICATIONS

"U.S. Appl. No. 16/927,259, Non Final Action dated Dec. 27, 2021", 15 pgs.

(Continued)

*Primary Examiner* — Larry E Waggle, Jr.
(74) *Attorney, Agent, or Firm* — Schwegman Lundberg & Woessner, P.A.

(57) ABSTRACT

Implant positioning devices for use with and assisting in positioning orthopaedic fixation devices (such as bone plates, etc.). An implant positioning device may include a body that has a fastener guide with slits in a first end of the fastener guide that form a retaining arm proximal to the first end of the fastener guide. The implant positioning device may also be coupled to a bone plate by a retaining beam positioned within the implant positioning device to facilitate ease of alignment and insertion of the fastener into a fastener apertures of the bone plate.

21 Claims, 33 Drawing Sheets

(56) References Cited

U.S. PATENT DOCUMENTS

| | | |
|---|---|---|
| 2009/0024132 A1 | 1/2009 | Blain et al. |
| 2009/0076554 A1 | 3/2009 | Huebner et al. |
| 2009/0157086 A1 | 6/2009 | Digeser et al. |
| 2010/0234895 A1 | 9/2010 | Hess |
| 2016/0051297 A1 | 2/2016 | Steffensmeier et al. |
| 2020/0337751 A1 | 10/2020 | Detweiler et al. |

FOREIGN PATENT DOCUMENTS

| | | |
|---|---|---|
| JP | 2021511188 A | 5/2021 |
| WO | WO-2019143690 A1 | 7/2019 |

OTHER PUBLICATIONS

"U.S. Appl. No. 16/927,259, Notice of Allowance dated May 9, 2022", 5 pgs.

"U.S. Appl. No. 16/927,259, Response filed Apr. 27, 2022 to Non Final Office Action dated Dec. 27, 2021", 12 pgs.

"European Application Serial No. 19740708.3, Extended European Search Report dated Jan. 4, 2022", 9 pgs.

"International Application Serial No. PCT/US2019/013805, international Preliminary Report on Patentability dated Jul. 30, 2020", 10 pgs.

"International Application Serial No. PCT/US2019/013805, International Search Report dated Mar. 26, 2019", 2 pgs.

"International Application Serial No. PCT/US2019/013805, Written Opinion dated Mar. 26, 2019", 8 pgs.

\* cited by examiner

IMPLANT POSITIONER AND STERNAL PLATING SYSTEM

CROSS REFERENCE TO RELATED APPLICATIONS

This is a continuation of PCT application No. PCT/US2019/013805, entitled "IMPLANT POSITIONER AND STERNAL PLATING SYSTEM", filed Jan. 16, 2019, which is incorporated herein by reference. Application No. PCT/US2019/013805 claims the benefit of U.S. Provisional Patent Application Ser. No. 62/619,261, entitled "IMPLANT POSITIONER AND STERNAL PLATING SYSTEM", filed Jan. 19, 2018, which is incorporated herein by reference.

BACKGROUND OF THE INVENTION

1. Field of the Invention

The disclosure relates generally to implant positioning apparatuses and devices. More particularly, the disclosure relates to implant positioning apparatuses and devices for use in bone fixation, sternum fixation, and other orthopaedic fixation procedures.

2. Description of the Related Art

In some surgical procedures involving bones, for instance, the procedure may involve separating a bone into portions, which are thereafter reunited. This happens, for example, in entries into the chest cavity, as for heart surgery, where the sternum is required to be separated along its length. There may be other instances where a bone has undergone fracturing through some trauma, and is thereafter to have portions rejoined for proper healing. Additionally, in applications involving the spine, there may be independent bones that benefit from holding a particular position relative to each other to allow for healing of the disc and other surrounding tissues.

The bones or skeletal tissue, or combinations of bone and tissue, can be held secure to one another in adjacency using a fixation device, or system. Many kinds of conventional fixation devices include wires or cables that are organized to pull the bone portions together, laterally across a divide or fracture. However, these types of fixation devices can be relatively complex to emplace. For instance, if a plate-type structure is to be attached to a bone, it is important to locate the fixation points (e.g., for screws) very accurately, as for drilling pilot holes for the screws. Plainly, speed and ease in then attaching the structure are significant considerations.

SUMMARY OF THE INVENTION

Implant fixation devices and implant positioning devices are disclosed for assisting in positioning orthopaedic fixation devices (such as bone plates, etc.) for use in bone fixation, sternum fixation, and other orthopaedic fixation procedures. In an embodiment, an implant positioning device includes a body with fastener guides. The fastener guides include retaining arms formed at a proximal end of the fastener guide. The retaining arms are configured to releasably hold a fastener in the fastener guide such that a head of the fastener is exposed at a proximal end and engageable by a fastener driver. The implant positioning device also includes a through-bore formed in the body at the proximal end and a retaining beam inserted into the through-bore. The beam extends past or beyond a distal end of the body. The implant positioning device may also include a first recess formed on the body and configured to receive a handle. In addition, the implant positioning device may also include a second recess formed at the distal end of body with rails configured to prevent movement of an orthopaedic fixation device coupled to the implant positioning device.

In another embodiment, an implant positioning device is disclosed, wherein a plate is to be affixed to a bone. In this embodiment, the device includes an implant positioning device releasably coupled to the plate. The implant positioning device includes a through-bore formed in the body at the proximal end and a retaining beam inserted into the through-bore. The beam extends past or beyond a distal end of the body. The implant positioning device may also include a first recess formed on the body and configured to receive a handle. In addition, the implant positioning device may also include a second recess formed at the distal end of body with rails configured to prevent movement of an orthopaedic fixation device coupled to the implant positioning device. The device may also include a handle releasably coupled to the first recess. The handle includes a first end for gripping by a user of the device and a second end that includes a leaf spring engageable with the first recess to releasably couple the handle to the device.

BRIEF DESCRIPTION OF THE DRAWINGS

Embodiments of devices, systems, and methods are illustrated in the figures of the accompanying drawings which are meant to be exemplary and not limiting, in which like references are intended to refer to like or corresponding parts, and in which.

DETAILED DESCRIPTION OF THE INVENTION

While the embodiments described hereinafter are in the environment of positioning devices, systems and methods for use in positioning orthopaedic fixation devices for bones and other body parts, it should be appreciated that the disclosure has broader application, such as other calcaneus body parts require fixation features, such as screws, pins, or other fastener, to be located and placed.

Figure 1:
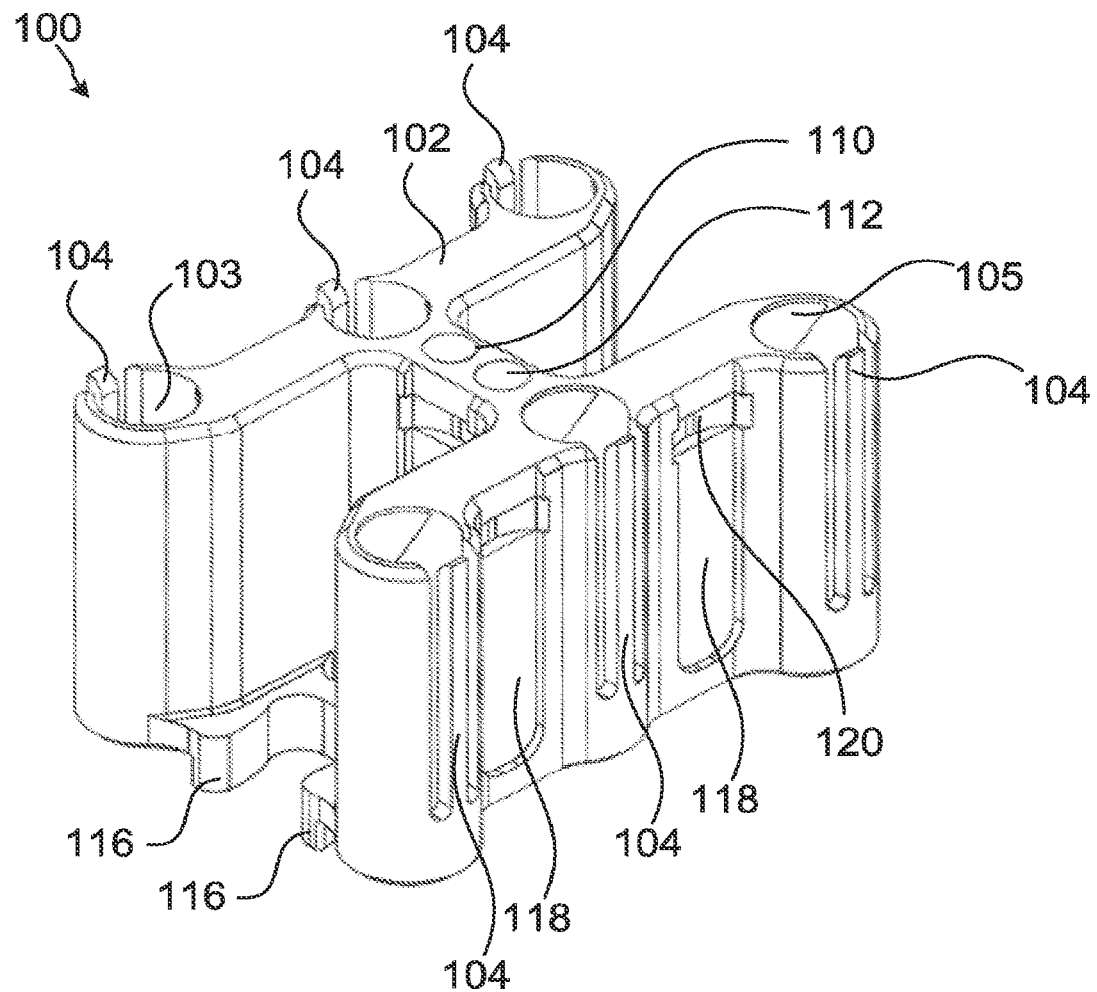
FIG. 1 illustrates a first perspective view of an implant positioning device in accordance with an embodiment of the disclosure.
Figure 2:
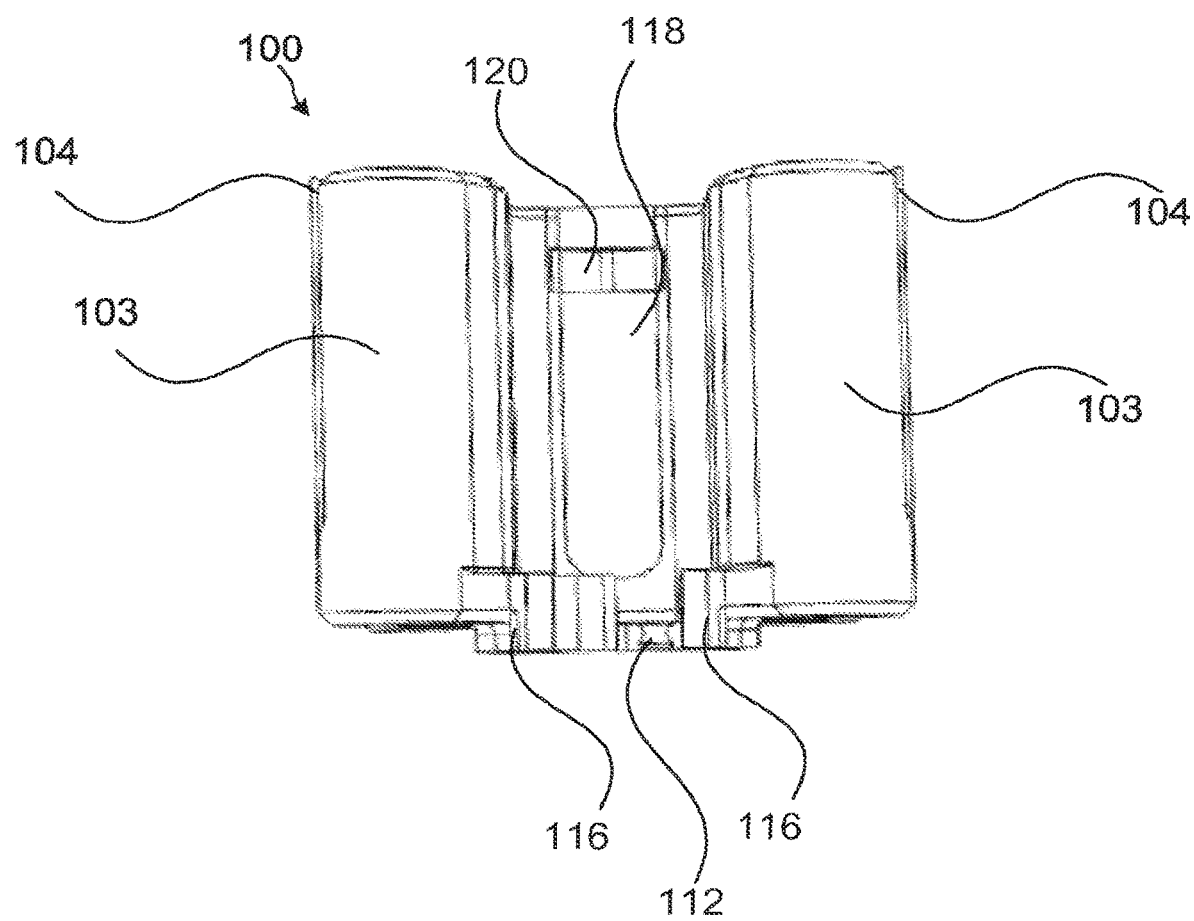
FIG. 2 illustrates a first side view of the implant positioning device of FIG. 1 in accordance with an embodiment of the disclosure.
Figure 3:
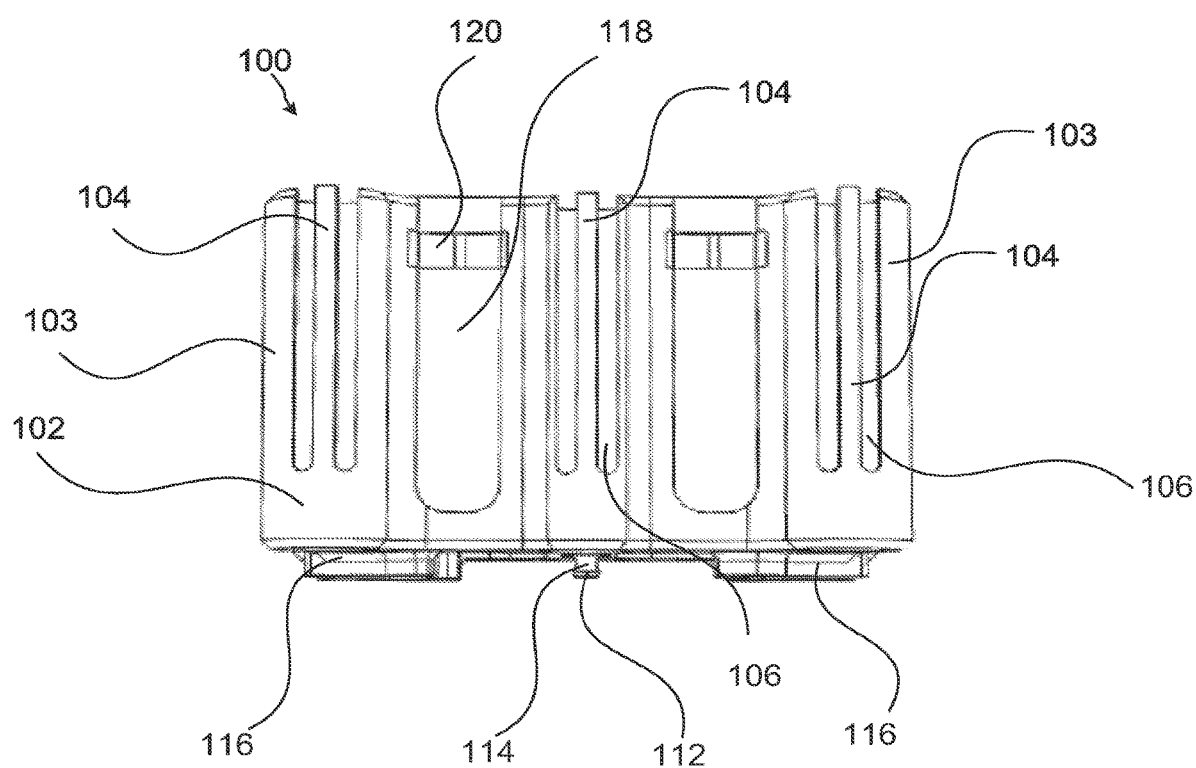
FIG. 3 illustrates a second side view of the implant positioning device of FIG. 1 in accordance with an embodiment of the disclosure.

FIGS. 1-4 illustrate an implant positioning device 100 for use with an implant fixation device, such as a plate, according to an embodiment of the disclosure. As illustrated in FIG. 1, the implant positioning device 100 includes a frame or a body 102 with one or more fastener guides 103. Each fastener guide 103 includes one or more retaining arms 104 (which may be finger-like structures) formed on a first end or proximal end of the fastener guide 103 by slits or apertures 106. The retaining arm 104 is configured to releasably hold, guide, and position a fastener that may be used to couple an orthopaedic fixation device, such as a plate, to a bone or other body part. Each fastener guide 103 may also include an angled surface 105 formed inside the fastener guide 103 at the proximal or top end of the fastener guide 103. The angled surface 105 facilitates insertion and positioning of a fastener in the guide 103. The angled surface 105 may also form a lip at the proximal or top end of the fastener guide 103 that retains a fastener in the fastener guide 103 and reduces the risk of a fastener falling out of the fastener guide 103 if the positioning device 100 is tilted or turned upside down.

The proximal end of the implant positioning device 100 also allows a top of the fastener to be exposed. This allows access for a fastener driver to access and engage a head of the fastener. The fastener may be a screw, pin, rivet, and other type of fastener, etc., and the retaining arm 104 and slits 106 may serve as expansion zones to help capture a wide variety of fasteners effectively. As illustrated, the slits 106 are positioned on opposing sides of the retaining arm 104. The slits 106 also allow the retaining arm 104 to elastically move or flex away from the guide 103 to allow the fastener to be moved or pushed through the fastener guide 103, when the fastener is driven into a bone or other body part.

As illustrated in FIG. 1, the implant positioning device 100 may include six fastener guides 103. However, the implant positioning device 100 may include more or less than six fastener guides 103 as needed to reattach bones after a sternotomy or other procedure. The retaining arms 104 may also be used to guide other instruments, for example, drills/drill bits, marking instruments to place markings, pegs, headless pins, etc. in a bone, which then serve as locating features to place plates or any other device before or after a resection is made, or after a fracture occurs.

In addition, the body 102 may include one or more lumens, boreholes, channels or through-bores 110 extending through the body 102 from the first/proximal end of the implant positioning device 100 to a second/distal end of the implant positioning device 100. Each through-bore 110 is configured to receive a retaining beam 112. The retaining beam 112 may be inserted into the corresponding through-bore 110 and retained within the through-bore 110 by being press-fit within the through-bore 110. The retaining beam 112 may be welded at the first/proximal end of the body 102 to ensure the retaining beam 112 remains within the through-bore 110. However, the retaining beams 112 may also be inserted into the through-bores 110 using a number of different methods. For example, the retaining beams 112 may be screwed into the through-bores 110 using threads that are formed on the proximal end of the retaining beam and through-bore.

Figure 5:
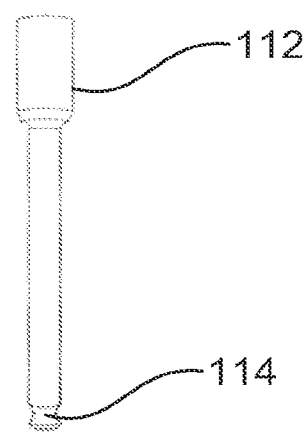
FIG. 5 illustrates a retaining beam for the implant positioning device of FIG. 1 in accordance with an embodiment of the disclosure.

Each retaining beam 112, as shown in more detail in FIG. 5, is configured to removably couple the implant positioning device 100 to a plate, such that the implant positioning device 100, such that a fastener disposed within the implant positioning device 100 is in alignment with a fastener aperture in a plate 200. While two retaining beam 112 are illustrated, the implant positioning device 100 may have additional or fewer retaining beams 112 as needed, to removably couple the fastener guide 100 with the plate 200.

Each retaining beam 112 has a first or proximal portion that is substantially the same size as a diameter of the through-bore 110 to ensure the retaining beam 112 can be press-fit into the through-bore 110. The retaining beam 112 also has a second or distal portion that is opposite the first/proximal portion that has a diameter less than the diameter of the first portion. The smaller second portion of the retaining beam 112 allows the retaining beam to flex within the through-bore 110 to removably couple with a plate. In addition, the through-bore 110 may prevent the retaining beam 112 from becoming, deformed due to over flexing.

Figure 7:
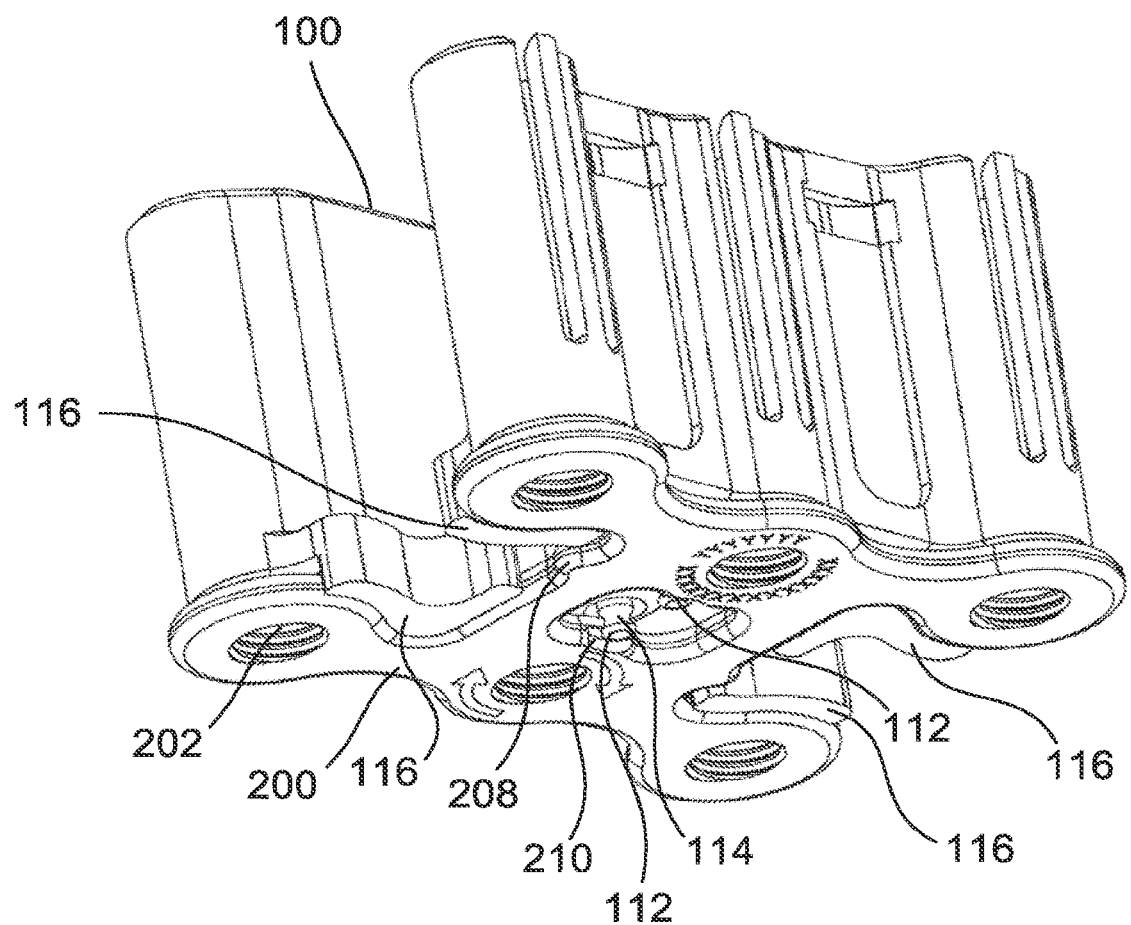
FIG. 7 illustrates a perspective view of the implant positioning device of FIG. 1 aligned with the plate of FIG. 6 in accordance with an embodiment of the disclosure.

Further, the second end has a retaining beam channel 114 formed around the retaining beam 112 to receive a side of a plate. The retaining beam channel 114 may be shaped to reflect a shape of the side of the plate to be received to removably couple the implant positioning device 100 to the plate, as shown in FIG. 7.

According to one embodiment, the body 102 may have a substantially H-shape, and the through-bores 110 and retaining beams 112 may be positioned in the horizontal between the legs of the "H". However, the body 102 may be shaped in a number of different ways to match a shape of a plate to be used. For example, during a median sternotomy, a vertical inline incision is made along a sternum of a patient and the sternum is divided along this incision. The implant positioning device 100 may be used to attach a plate that is substantially H-shaped (shown in FIG. 6) to reattach the sternum of the patient once the procedure is complete.

Figure 4:
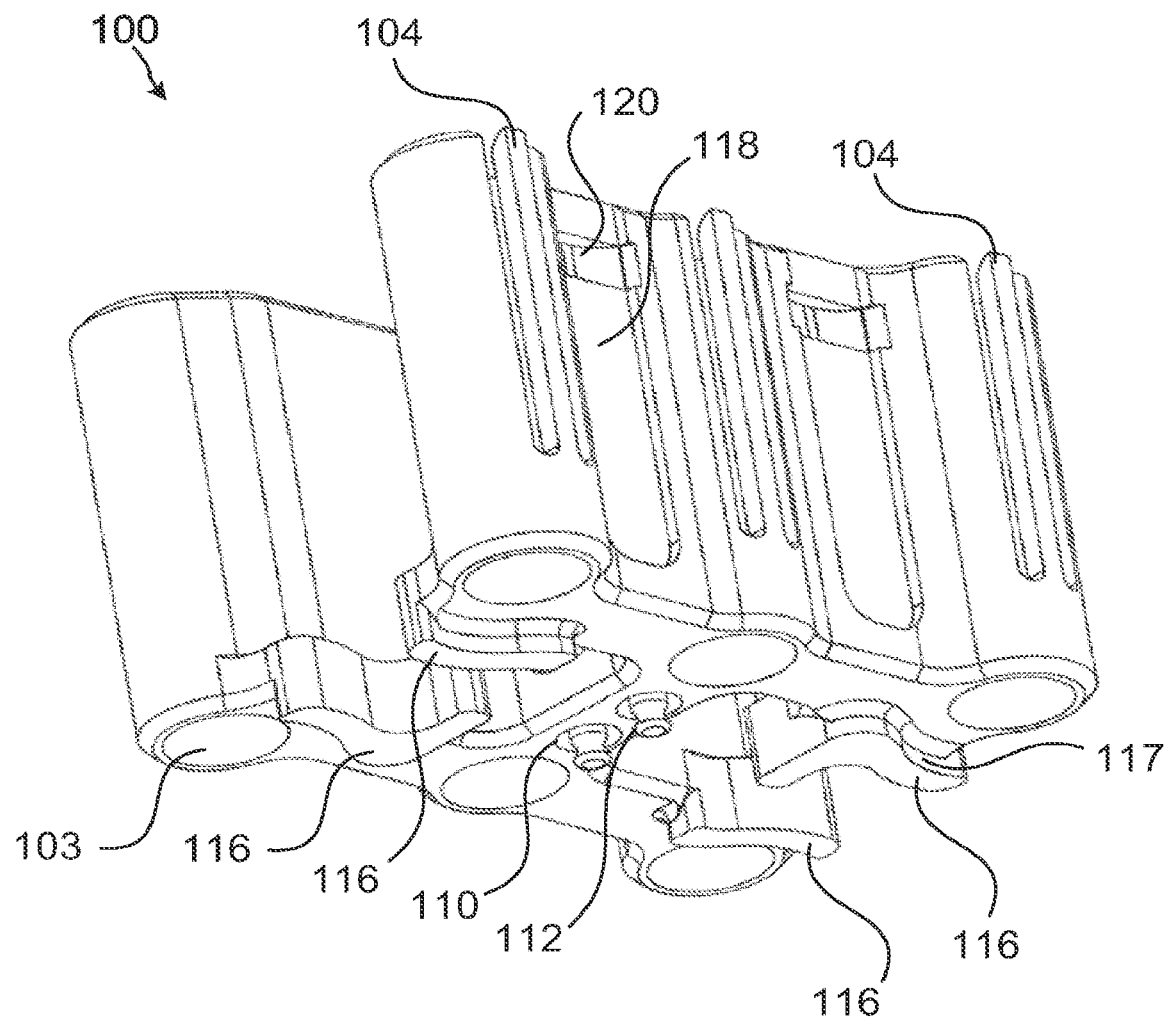
FIG. 4 illustrates a second perspective view of the implant positioning device of FIG. 1 in accordance with an embodiment of the disclosure.

The implant positioning device 100 may also include rails 116 (as shown in FIG. 4) that extend from the second/distal side of the body 102 proximal to an inner side of the legs of the H-shaped body 102. The rails 116 may be contoured to a shape of the plate and used to couple the implant positioning device 100 to the plate and prevent the plate from spinning and/or angular or rotational movement of the plate when removably coupled to the implant positioning device 100. Multiple rails 116 may be used to help position the plate in the proper orientation for attachment onto a hone or other body part. In addition, each rail 116 may also have a rail channel 117 adapted to receive an edge of the plate to removably couple the plate to the implant positioning device 100 and further limit movement of the plate, as show in FIG. 7.

The body 102 may also have one or more handle recesses 118. The handle recesses 118 are configured to receive and removably couple a handle 124 (shown in FIG. 8) to the implant positioning device 100. The handle recesses 118 may help prevent rotation of the implant positioning device 100 when attached to the handle 124. As illustrated, handle recesses 118 may be positioned between two adjacent fastener guides 103 on an exterior side of the body 102 and may also be positioned in a middle portion of the H-shaped body. The handles recesses 118 may also have secondary recesses 120 to provide an additional connection point for the handle 124. For example, the secondary recesses 120 may provide a connection point that rigidly attaches the handle 124 to the body 102.

According to one aspect of the disclosure, the implant positioning device 100 may be disposable or reusable, and pre-loaded with fasteners. Additionally, the body 102 may be made of a semi-elastic material such that the retaining arms 104 and retaining beams 112 are able to expand without substantial deformation, such as a metal, polymer, plastic, etc. For example, the body 102 may be made of a metal material that allows the retaining arms 104 and retaining beams 112 to expand without substantial deformation.

Figure 6:
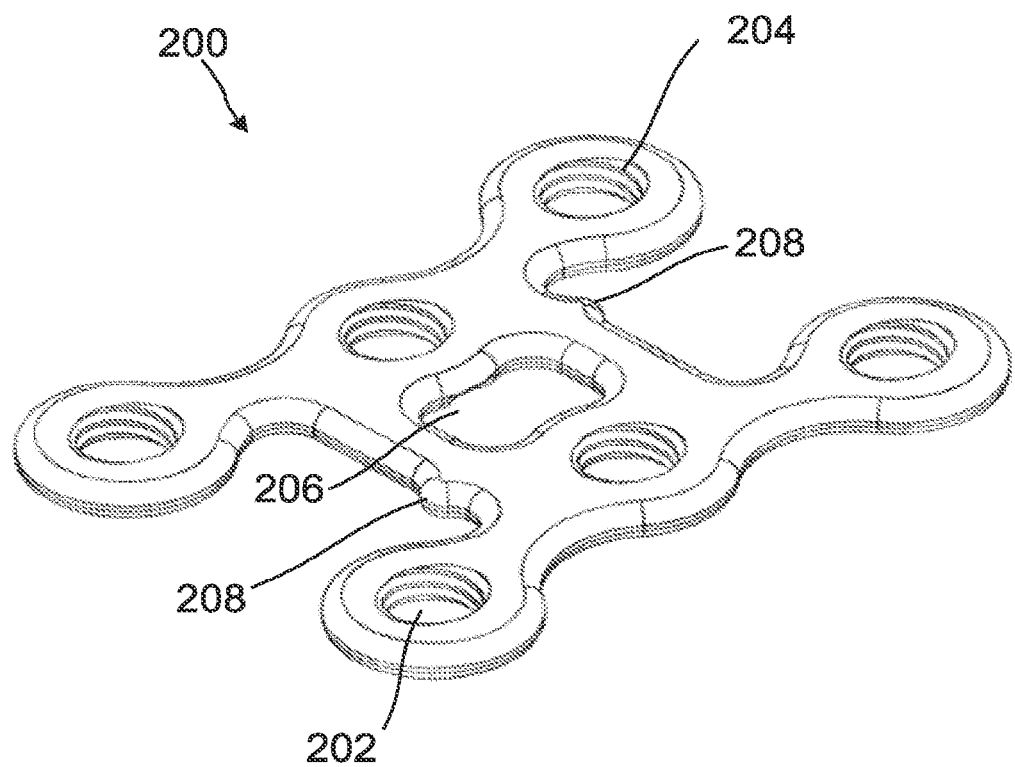
FIG. 6 illustrates a perspective view of a plate for an implant positioning device in accordance with an embodiment of the disclosure.

FIG. 6 illustrates a plate 200 that is attachable to a bone. The plate 200 includes one or more fastener apertures 202, each with grooves or threads 204 configured to receive a fastener to couple the plate 200 to a bone. The plate 200 includes an aperture 206 that is substantially in the middle of the plate 200. The aperture 206 may be configured to receive the retaining beams 112 of the implant positioning device 100 to removably couple the implant positioning device 100 to the plate 200. For example, as show tin FIG. 7, each retaining beam 112 may have a channel 114 and a side of the plate 200 forming the aperture 206 may be configured to fit within the channel 114 to removably couple the implant positioning device 100 to the plate 200. The plate 200 may also include protrusions 208 that extend from a middle portion of the plate 200. The protrusions 208 may be keyed to the implant positioning device 100 and used to prevent the plate 200 from being coupled to the implant positioning device 100 in an incorrect orientation, i.e., upside down.

In one example, the implant positioning device 100 may be preloaded with a fastener by placing the fastener in the first end of the fastener guide 103. This may include pushing the fastener into the fastener guide 103 until a head of the fastener is gripped and held in place by the retaining arms 104. The implant positioning device 100 may then be coupled to a plate, such as plate 200, by pushing the retaining beams 112 of the implant positioning device 100 onto the plate 200. This may cause the retaining beams 112 to move or flex, and then snap onto the side of the plate 200, for example, into cutouts or recesses 210 formed in the plate 200. The cutouts or recesses 210 may be keyed to receive the retaining beams 112 and couple the plate 200 to the implant positioning device 100. It should be appreciated that the implant positioning device 100 may be coupled to a plate, such as plate 200, prior to the insertion of the fastener.

Once the implant positioning device 100 is coupled to the plate 200 and the fastener is inserted into the fastener guide 103, the implant positioning device 100 may provide a type of handle or holding zone that can be gripped by a user or other instrument. This allows the plate 200 to be positioned on a bone or other body part. Referring to FIG. 7, the retaining beams 112 couple to the inner profile of the plate 200 within the aperture 206, and an outer peripheral shape of the implant positioning device 100 is smaller than an outer peripheral shape of the plate 200. This allows the entire periphery of the plate 200 to be visible when the implant positioning device 100 is coupled to the plate 200. Accordingly, the peripheral shapes of the plate 200 and the implant positioning device 100 allow a user to view where the plate 200 is ultimately going to be placed in relation to the bone, tissue, or other body part.

Once the plate 200 is positioned, the fastener can be driven through the fastener guide 103 and fastener aperture 202, and into the bone or other body part by a fastener driver to couple the plate 200 to the bone or other body part. As the fastener is driven through the fastener guide 103, the retaining arms 104 move or flexes away from the body 102 to allow the fastener to move through the fastener guide 103.

It should be appreciated that the implant positioning device 100 can be coupled to the plate 200 with the fastener guides 103 in alignment with the corresponding fastener apertures 202. This may facilitate ease of alignment and insertion of separate fasteners into each of the fastener apertures 202. It should also be appreciated that the size, shape, and number of fastener apertures of the plate can be modified and adapted for a specific application. Similarly, the implant positioning device 100 may be adapted or modified to accommodate different plate geometries and features. The implant positioning device 100 may be used in conjunction with any type of bone plate or other type of plate. For example, the implant positioning device 100 may be used for alignment and fixation of honey elements to prevent motion in a particular direction as well as providing dynamic stabilization. The implant positioning device 100 may also be used prior to or after a separation of a bone or other calcaneus body parts to align one or more plates.

Figure 8:
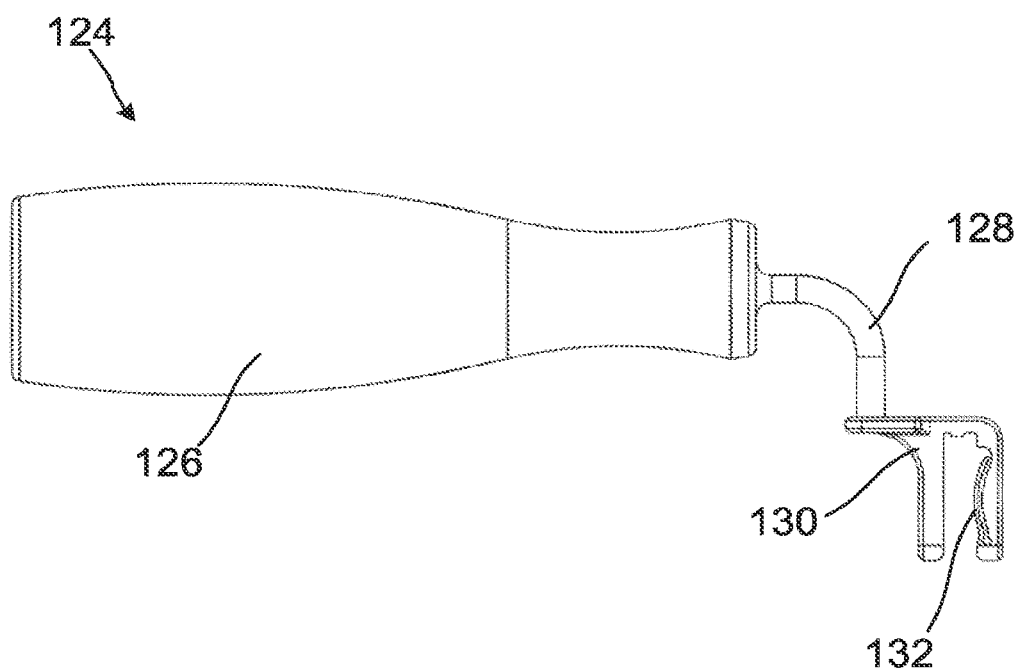
FIG. 8 illustrates a perspective view of a handle for use with the implant positioning device in accordance with an embodiment of the disclosure.
Figure 9:
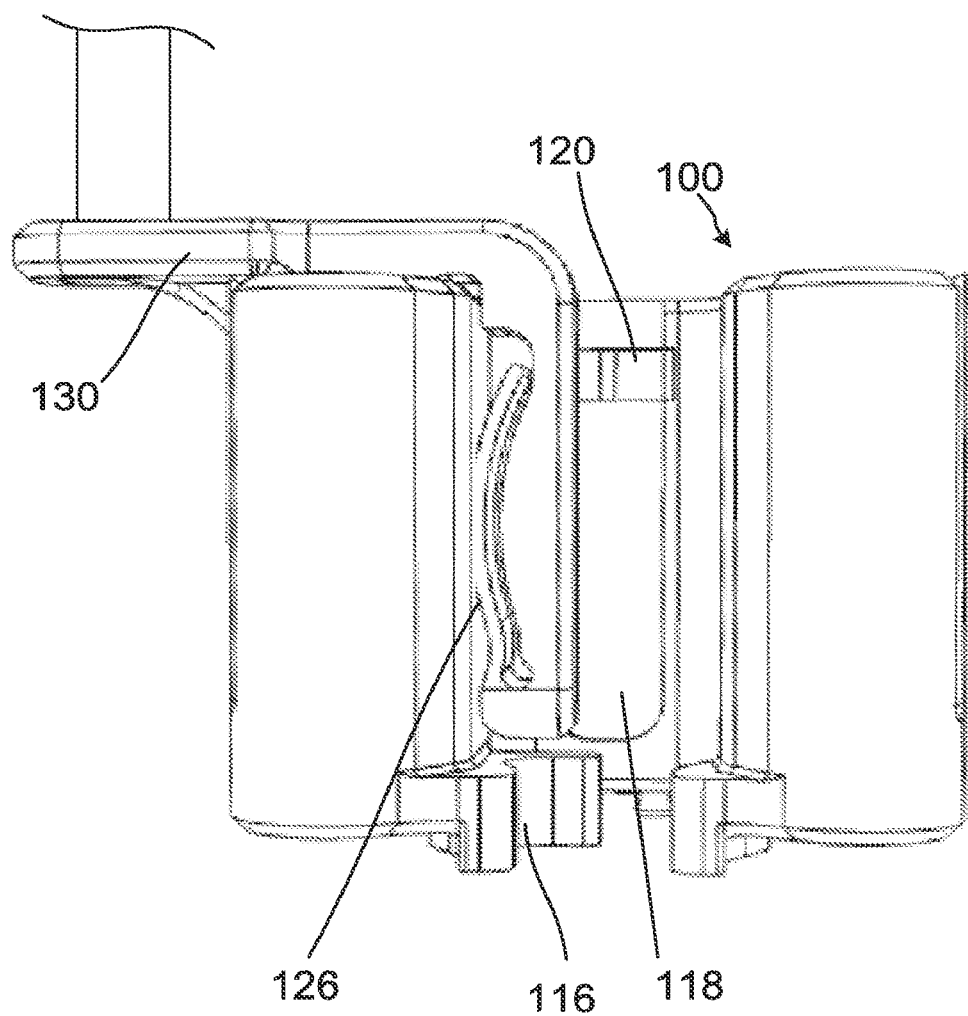
FIG. 9 illustrates a first perspective view of the implant positioning device of FIG. 1 aligned with the handle of FIG. 8 in accordance with an embodiment of the disclosure.
Figure 10:
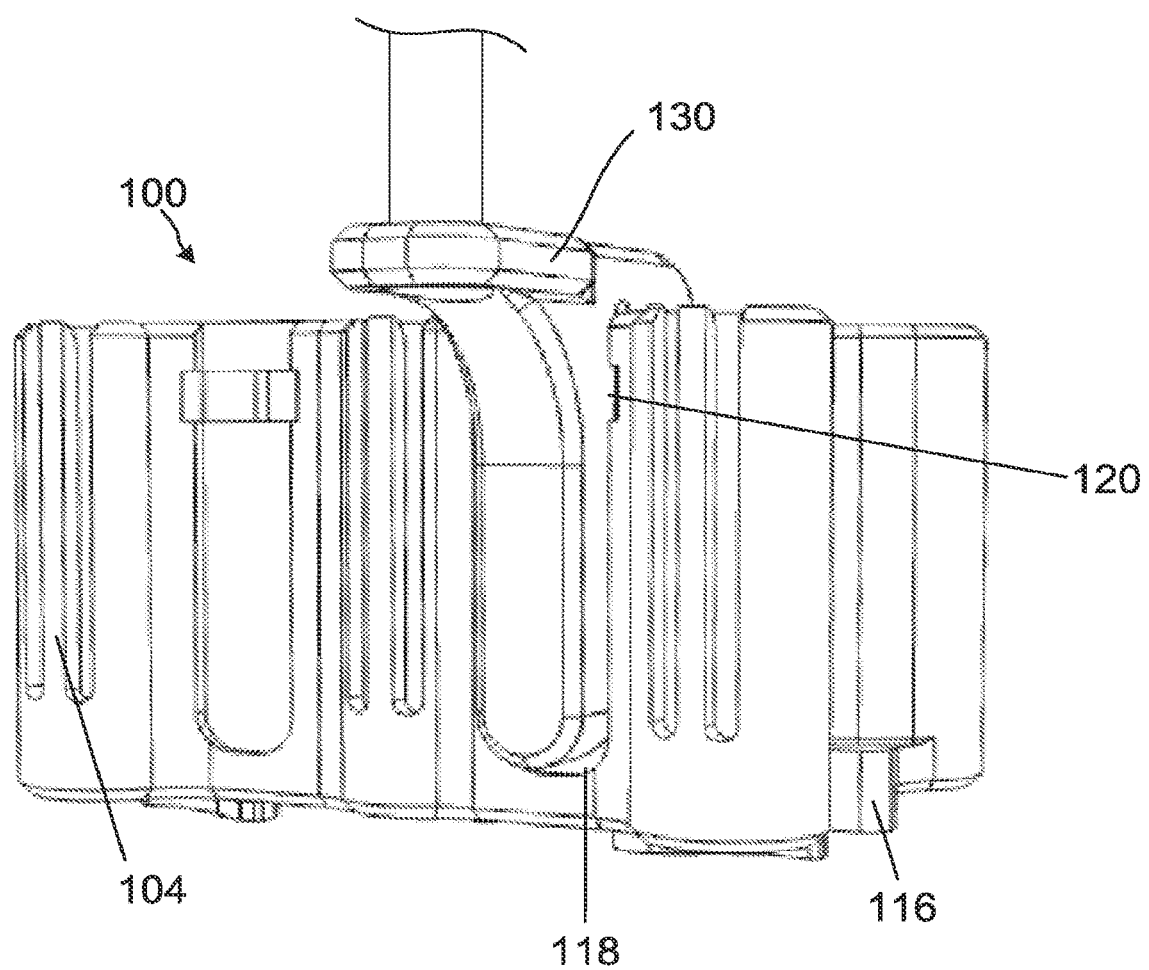
FIG. 10 illustrates a second perspective view of the implant positioning device of FIG. 1 aligned with the handle of FIG. 8 in accordance with an embodiment of the disclosure.

FIGS. 8-10 illustrate the handle 124 that may be coupled to the implant positioning device 100. The handle 124 includes a first end that has a gripping portion 126 that allows a user of the handle 124 to grip the handle. The gripping portion 126 is coupled to a connecting portion 128 that connects the gripping portion 126 to a head portion 130. The head portion 130 includes two prongs configured to fit around a body of an implant positioning device, for example implant positioning device 100.

The head portion 130 may be configured to slide into the handle recess 118 of the implant positioning device 100, as shown in FIGS. 9 and 10. The handle 124 may releasably couple to the implant positioning device 100 and the handle recess 118 may minimize movement of the implant positioning device 100 relative to the handle 124. This assists in ease of use of the implant positioning device 100 to properly position the plate 200 on the bone. Further, the head portion 130 may include a leaf spring 132 on at least one of the two prongs to assist handle 124 in coupling more securely to the body 102 of the implant positioning device 100 and further limit movement of the implant positioning device 100 relative to the handle 124. For example, when the handle 124 is coupled to the handle recess 118, the leaf spring 132 deforms and the leaf spring exerts a spring-force against the body 102. The deformation and spring-force provides a frictional engagement between the leaf spring 132 and the body 102 that retains the implant positioning device 100 on the handle 124.

Figure 11:
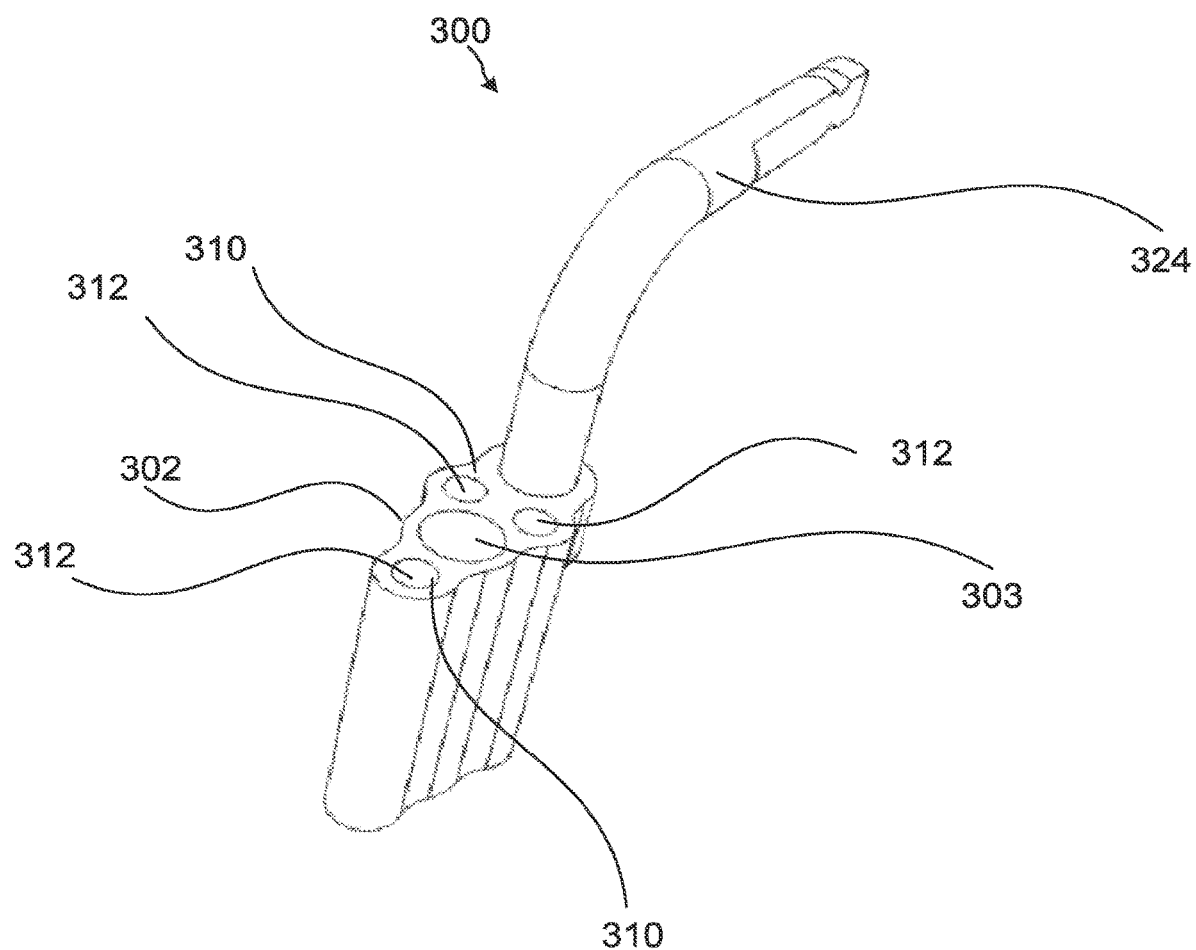
FIG. 11 illustrates a first perspective view of another implant positioning device in accordance with an embodiment of the disclosure.
Figure 12:
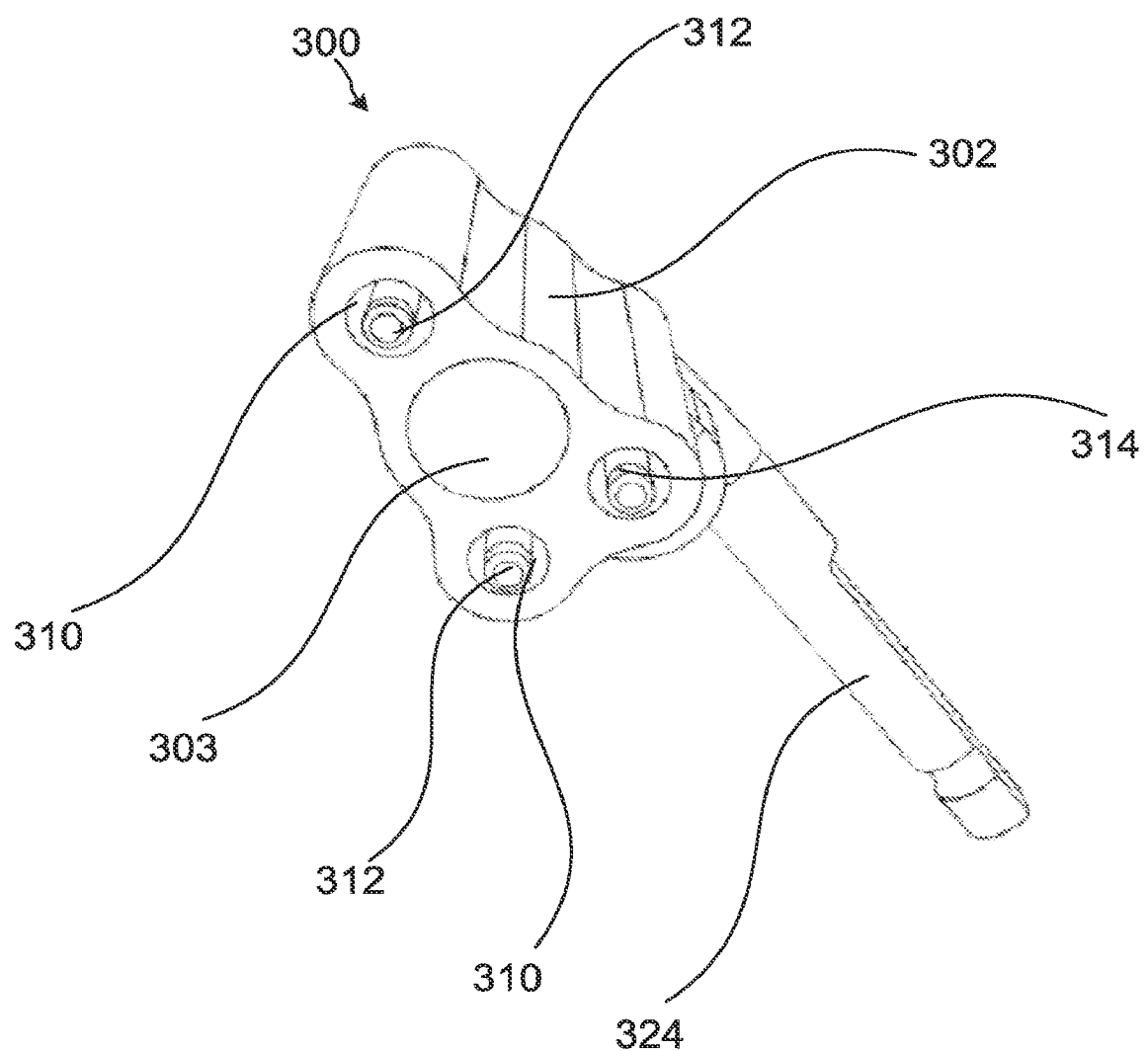
FIG. 12 illustrates a second perspective view of the implant positioning device of FIG. 11 in accordance with an embodiment of the disclosure.

FIGS. 11-15 illustrate an implant positioning device 300 for use with an implant fixation device according to an embodiment of the disclosure. As illustrated in FIG. 11, the implant positioning device 300 includes a frame or a body 302 that has one fastener guide 303. The fastener guide 303 is configured to releasably hold, guide, and position a fastener that may be used to couple an orthopaedic fixation device, such as a plate, to a bone or other body part. The proximal end of the implant positioning device 300 also allows a top of the fastener to be exposed. This allows access for a fastener driver to access and engage a head of the fastener. The fastener may be a screw, pin, rivet, and other type of fastener, etc. The fastener guide 303 may have expansion zones to help capture a wide variety of fasteners effectively. For example, the fastener guide 303 may include one or more retaining arms (which may be finger-like structures) formed by slits or apertures, as described above with respect to the implant positioning device 100.

As illustrated in FIG. 11, the implant positioning device 300 may include a single fastener guide 303. However, the implant positioning device 300 may include more than one fastener guide 303 as needed to reattach bones or other body parts. In addition, the fastener guide 303 may also be used to guide other instruments, for example, drills/drill bits, marking instruments to place markings, pegs, headless pins, etc. in a bone, which then serve as locating features to place plates or any other device before or after a resection is made, or after a fracture occurs.

The body 302 may include one or more lumens, boreholes, channels or through-bores 310 at the first/proximal end of the implant positioning device 300 that extend to a second/distal end opposite the first end. Each through-bore 310 is configured to receive a retaining beam 312. The retaining beam 312 may be inserted into the corresponding through-bore 310 and retained within the through-bore 310 by being press-fit within the through-bore 310. Further, the retaining beam 312 may be welded at the first/proximal end of the body 302 to ensure the retaining beam 312 remains within the through-bore 310. However, the retaining beams 312 may also be inserted into the through-bore 310 using a number of different methods. For example, the retaining beams 312 may be screwed into the through-bore 310 using threads that are formed on the proximal end of the retaining beam and through-bore.

The retaining beams 312, as described above and shown in more detail in FIG. 5, are configured to removably couple the implant positioning device 300 around a fastener aperture of a plate, such that the implant positioning device 300, or fastener disposed within the implant positioning device 300, is in alignment with a fastener aperture in the plate. While three retaining beams 312 are illustrated, the implant positioning device 300 may have additional or fewer retaining beams 312 as needed, to removably couple the fastener guide 303 with the plate.

Each retaining beam 312 has a first or proximal portion that is substantially the same size as a diameter of the through-bore 310 to ensure the retaining beam 312 can be press-fit into the through-bore 310. The retaining beam 312 also has a second or distal portion that is opposite the first/proximal portion that has a diameter less than the diameter of the first end. The smaller second portion of the retaining beam 312 allows the retaining beam to flex within the through-bore 310 to removably couple with a plate. In addition, the through-bore 310 may prevent the retaining beam 312 from becoming deformed due to over flexing.

Figure 13:
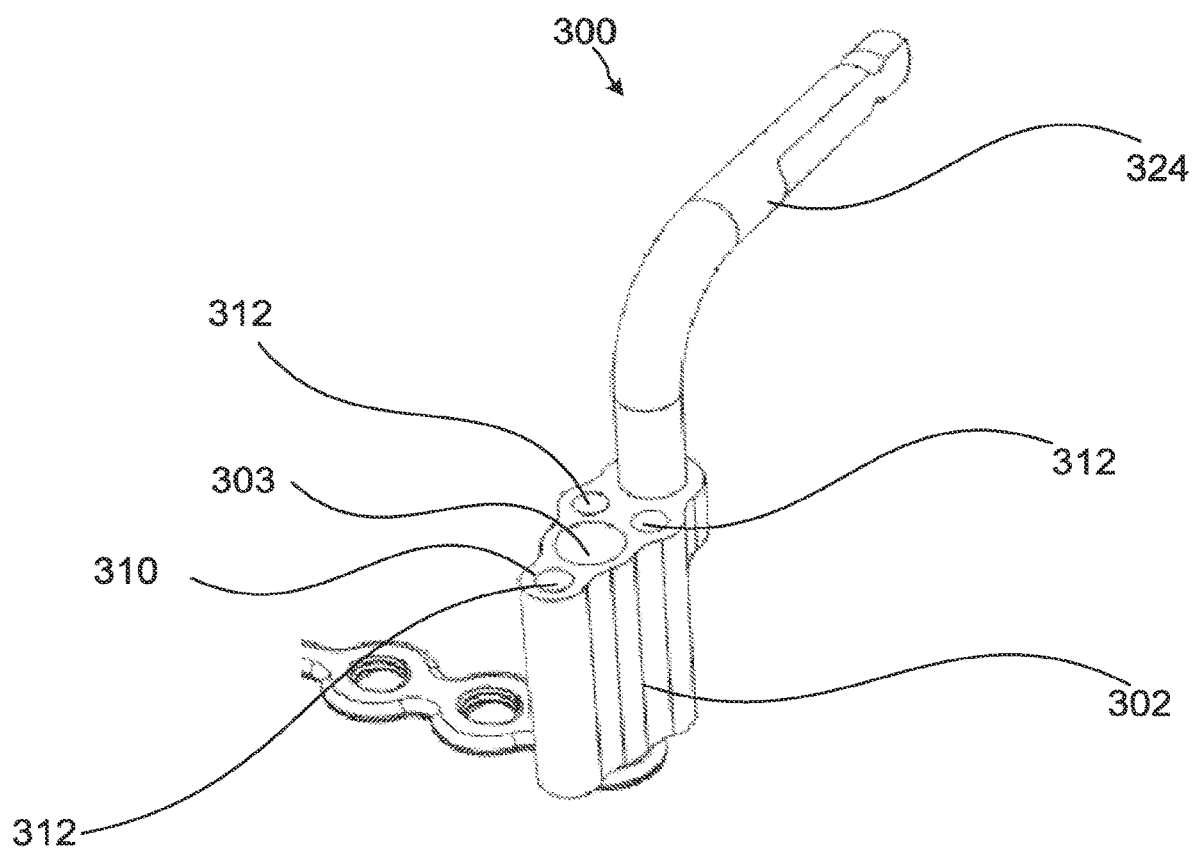
FIG. 13 illustrates a first perspective view of the implant positioning device of FIG. 11 aligned with a plate in accordance with an embodiment of the disclosure.
Figure 14:
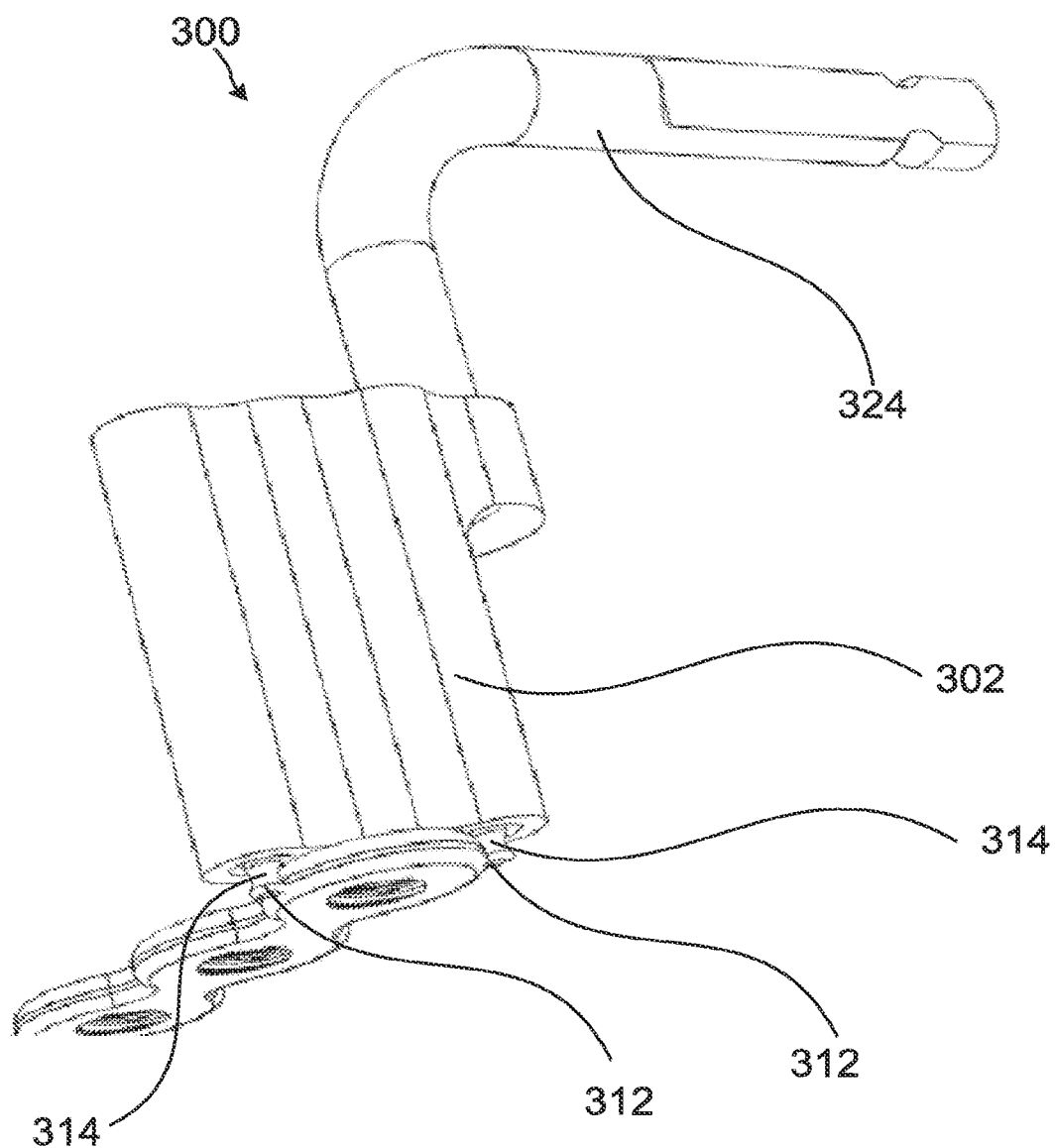
FIG. 14 illustrates a second perspective view of the implant positioning device of FIG. 11 aligned with a plate in accordance with an embodiment of the disclosure.
Figure 15:
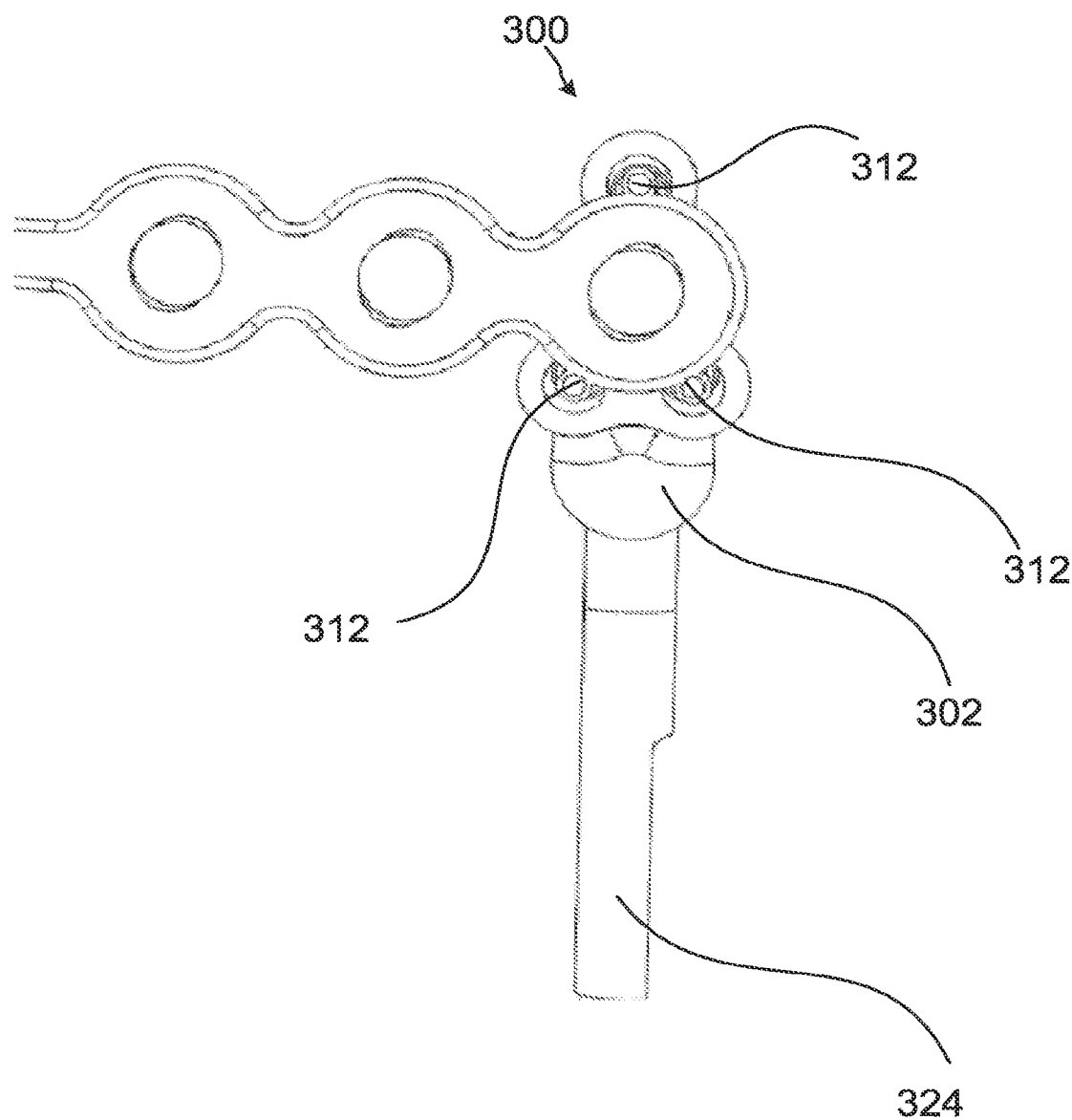
FIG. 15 illustrates a bottom view of the implant positioning device of FIG. 11 aligned with a plate in accordance with an embodiment of the disclosure.

Further, the second end has a retaining beam channel 314 formed around the retaining beam 312 to receive a side of a plate. The retaining beam channel 314 may be shaped to reflect a shape of the side of the plate to be received to removably couple the implant positioning device 300 to a plate, as shown in FIGS. 13-15.

According to one embodiment, the body 302 may have a substantially triangular shape. However, the body 302 may be shaped in a number of different ways to allow for implant positioning device 300 to removably couple around any fastener aperture on a plate, as illustrated in FIG. 13.

As described above with respect to the implant position device 100, the implant positioning device 300 may be disposable or reusable, and pre-loaded with fasteners. Similarly, the body 302 may be made of a semi-elastic material such that the fastener guide 303 is able to expand without substantial deformation.

The body 302 may also have a handle 324 that extends from the body 302 and is adapted to couple to a grip (not shown). The handle 324 may minimize movement of the implant positioning device 300. The handle 324 also assists in ease of use of the implant positioning device 300 to properly position a plate.

Figure 16:
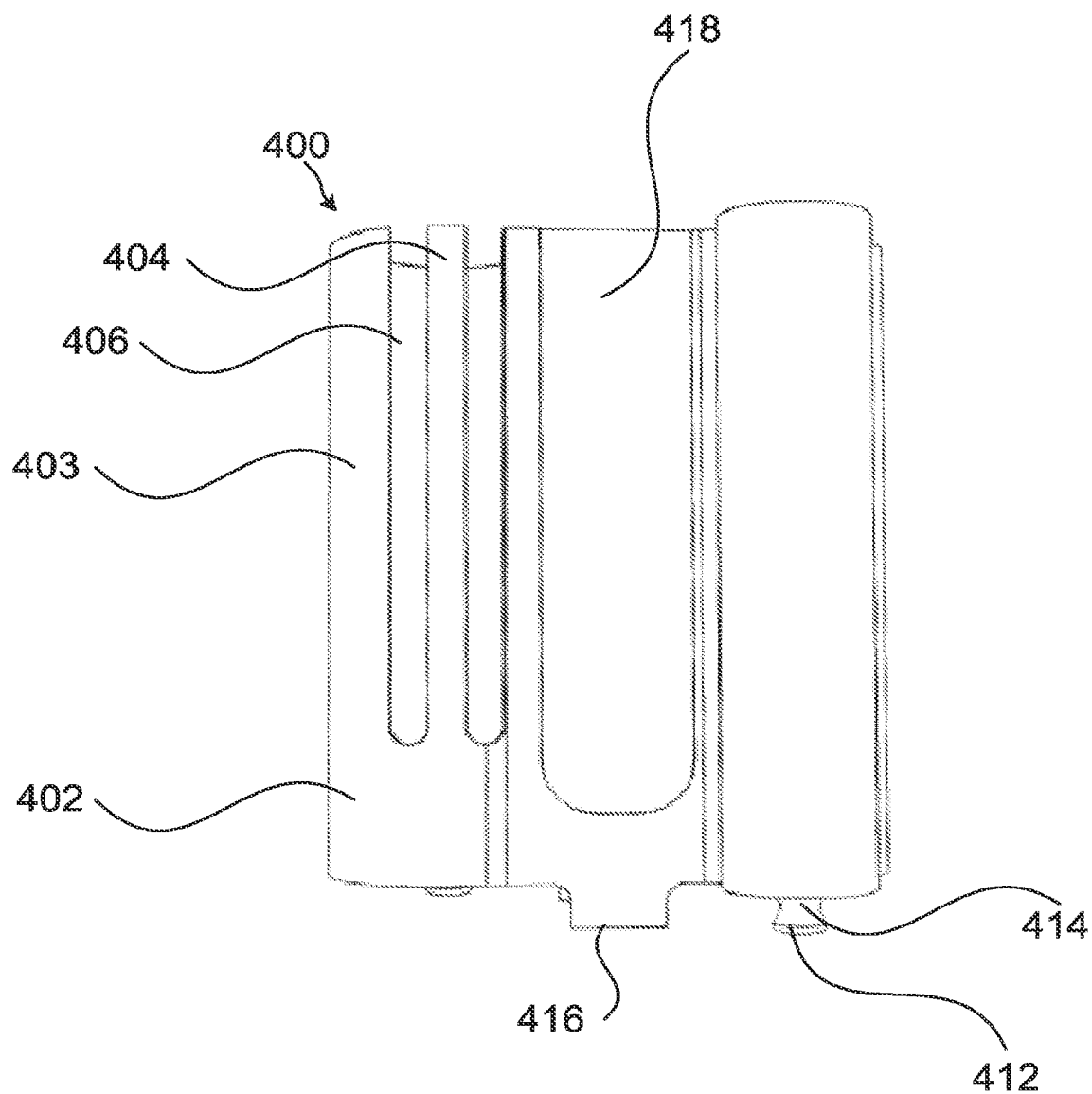
FIG. 16 illustrates a first perspective view of another implant positioning device in accordance with an embodiment of the disclosure.
Figure 17:
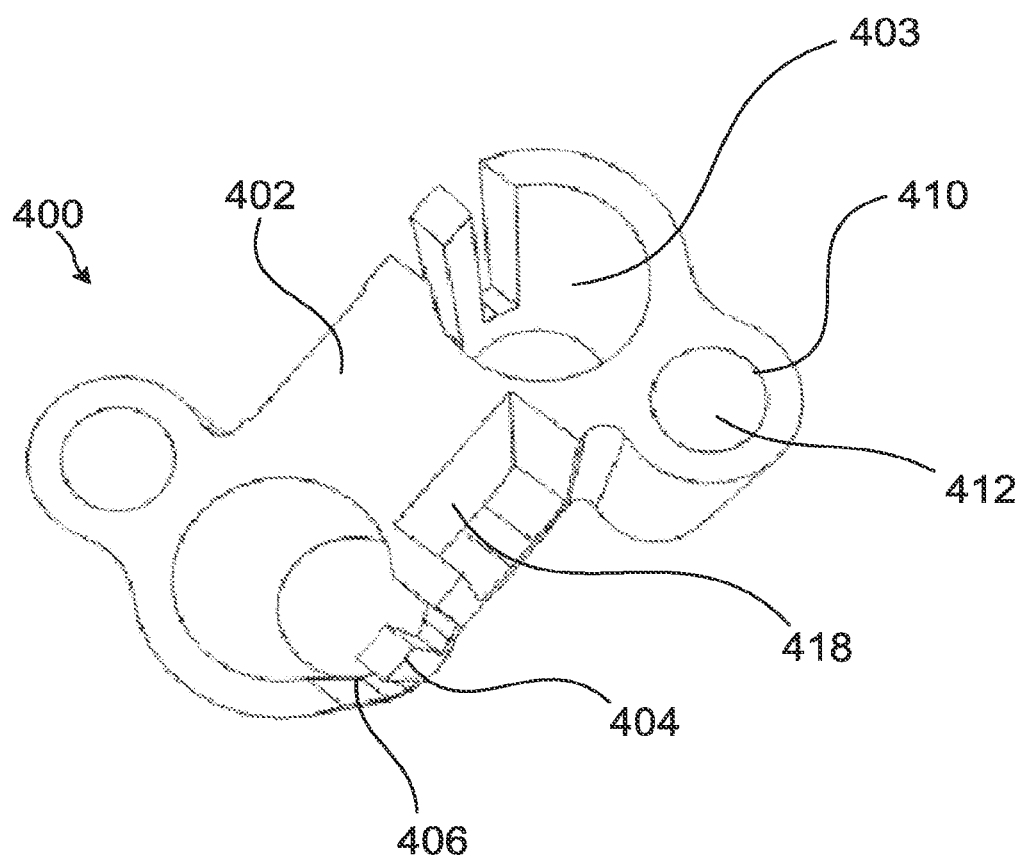
FIG. 17 illustrates a second perspective view of the implant positioning device of FIG. 16 in accordance with an embodiment of the disclosure.
Figure 18:
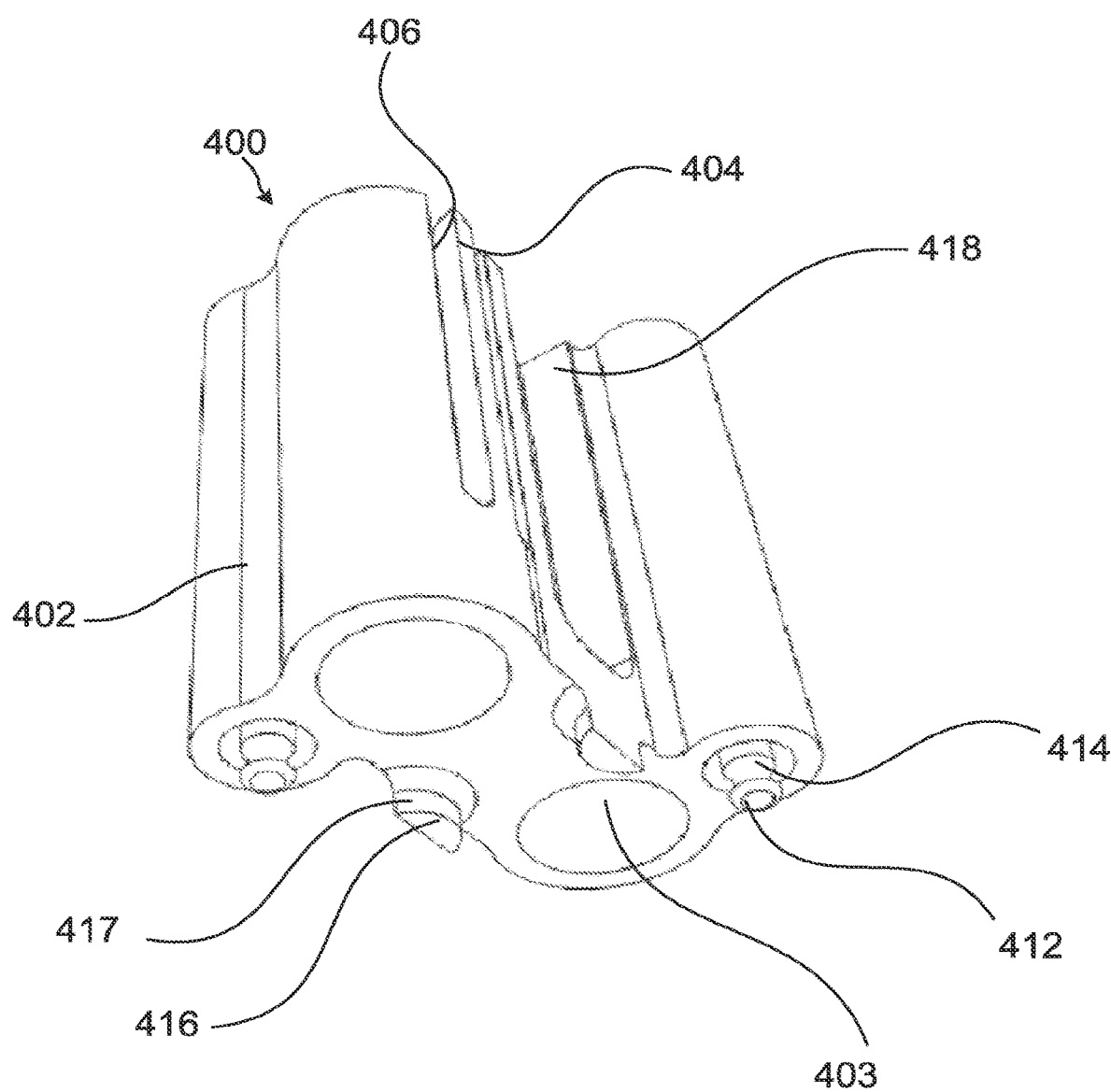
FIG. 18 illustrates a third perspective view of the implant positioning device of FIG. 16 in accordance with an embodiment of the disclosure.

FIGS. 16-18 illustrate another implant positioning device 400 for use with an implant fixation device according to another embodiment of the disclosure. As illustrated in FIG. 16, the implant positioning device 400 includes a frame or a body 402 that has fastener guides 403. Each fastener guide 403 includes one or more retaining arms 404 (which may be finger-like structures) formed on a first end or proximal end of the fastener guide 403 by slits or apertures 406. Each retaining arm 404 is configured to releasably hold, guide, and position a fastener that may be used to couple an orthopaedic fixation device, such as a plate, to a bone or other body part. The proximal end of the implant positioning device 400 also allows a top of the fastener to be exposed. This allows access for a fastener driver to access and engage a head of the fastener. The fastener may be a screw, pin, rivet, and other type of fastener, etc., and the retaining arm 404 and slits 406 may serve as expansion zones to help capture a wide variety of fasteners effectively. As illustrated, the slits 406 are positioned on opposing sides of the retaining arm 404. The slits 406 also allow the retaining arm 404 to elastically move or flex to allow the fastener to be moved or pushed through the corresponding fastener guide 403, when the fastener is driven into a bone or other body part.

As illustrated in FIG. 17, the implant positioning device 400 may include two fastener guides 403. However, the implant positioning device 400 may include more or less than two fastener guides 403 as needed to reattach bones after a sternotomy. The retaining arms 404 may also be used to guide other instruments, for example, drills/drill bits, marking instruments to place markings, pegs, headless pins, etc. in a bone, which then serve as locating features to place plates or any other device before or after a resection is made, or after a fracture occurs.

In addition, the body 402 may include lumens, boreholes, channels or through-bores 410 at the first/top end of the implant positioning device 400 that are disposed at opposite ends and sides from each other. The through-bores 410 are configured to receive a retaining beam 412, similar to one described above and shown in FIG. 5. Each retaining beam 412 may be inserted into the corresponding through-bore 410 and retained within the through-bore 410 by being press-fit within the through-bore 410. Further, the retaining beam 412 may be welded at the first/proximal end of the body 402 to ensure the retaining beam 412 remains within the through-bore 410. However, the retaining beam 412 may also be inserted into the through-bore 410 using a number of different methods. For example, the retaining beam 412 may be screwed into the through-bore 410 using threads that are formed on the proximal end of the retaining beam and through-bore.

The retaining beam 412 is configured to removably couple the implant positioning device 400 to a portion of a plate, such that the implant positioning device 400, or fastener disposed within the implant positioning device 400, is in alignment with a fastener aperture in the plate. While two retaining beams 412 are illustrated, the implant positioning device 400 may have additional or fewer retaining beams 412 as needed, to removably couple the fastener guide 400 with the plate.

Each retaining beam 412 has a first or proximal portion that is substantially the same size as a diameter of the through-bore 410 to ensure the retaining beam 412 can be press-fit into the through-bore 410. The retaining beam 412 also has a second or distal portion that is opposite the first/proximal end that has a diameter less than the diameter of the first portion. The smaller second portion of the retaining beam 412 allows the retaining beam to flex within the through-bore 410 to removably couple with a plate. In addition, the through-bore 410 may prevent the retaining beam 412 from becoming deformed due to over flexing.

Figure 19:
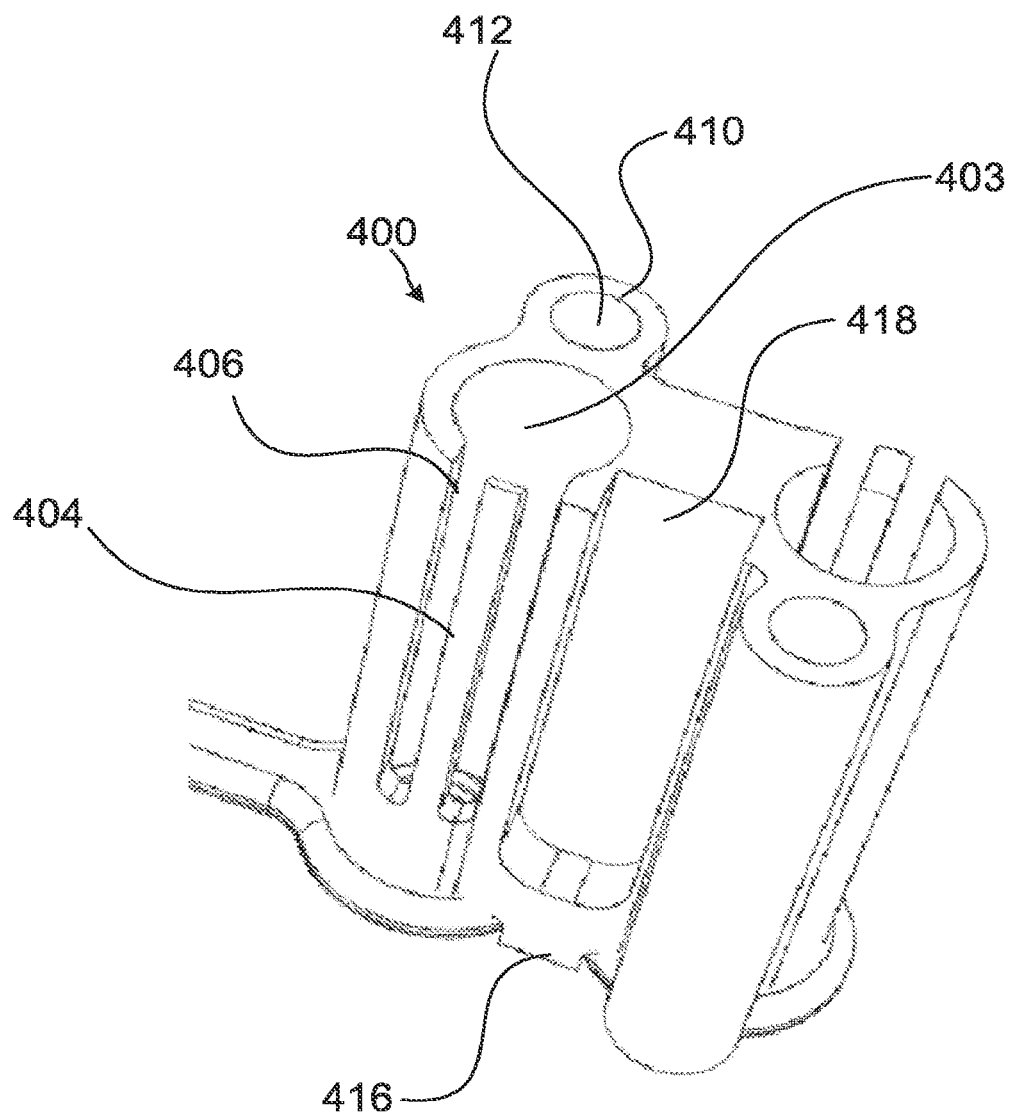
FIG. 19 illustrates a first perspective view of the implant positioning device of FIG. 16 aligned with a plate in accordance with an embodiment of the disclosure.
Figure 20:
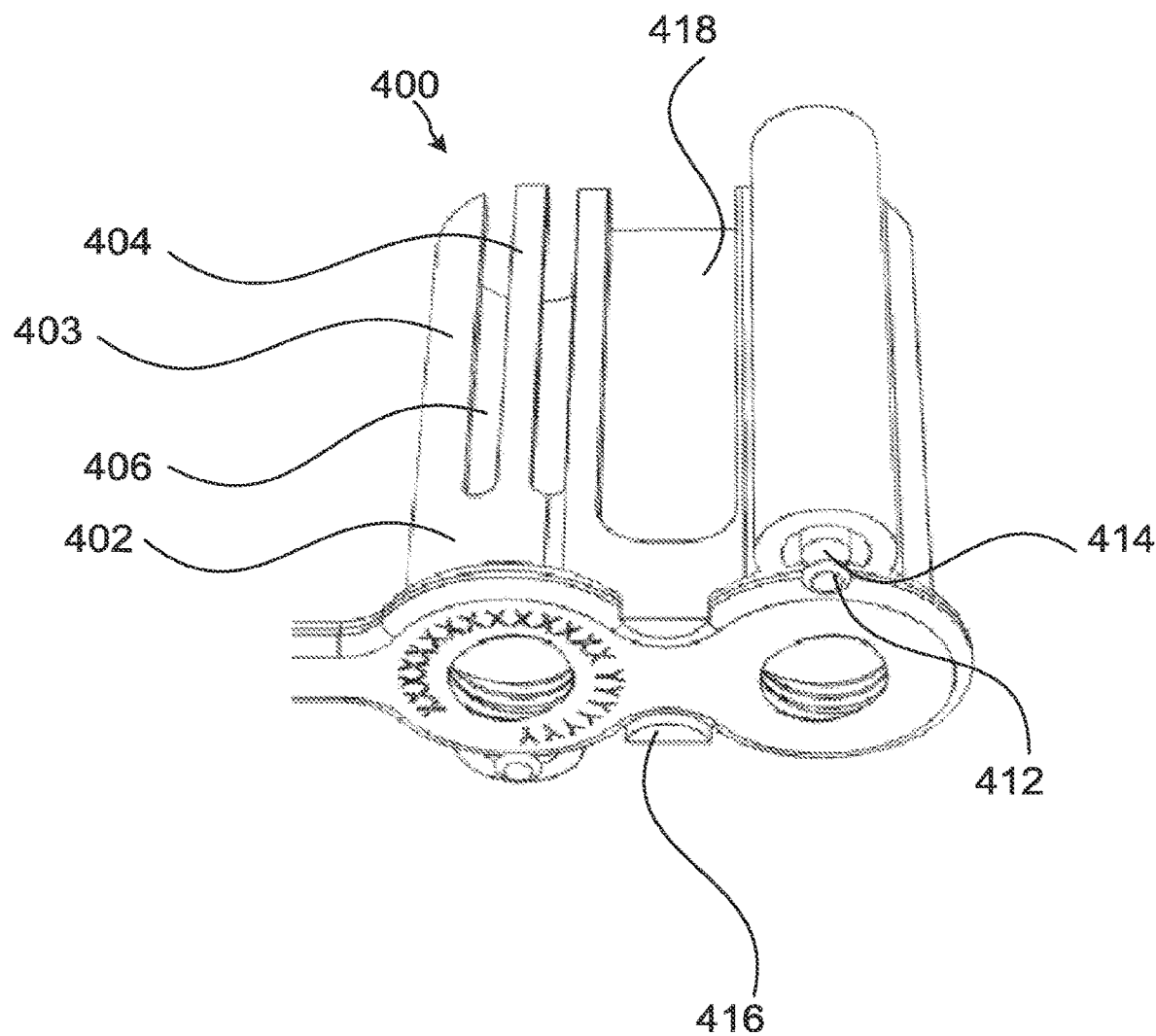
FIG. 20 illustrates a second perspective view of the implant positioning device of FIG. 16 aligned with a plate in accordance with an embodiment of the disclosure.
Figure 21:
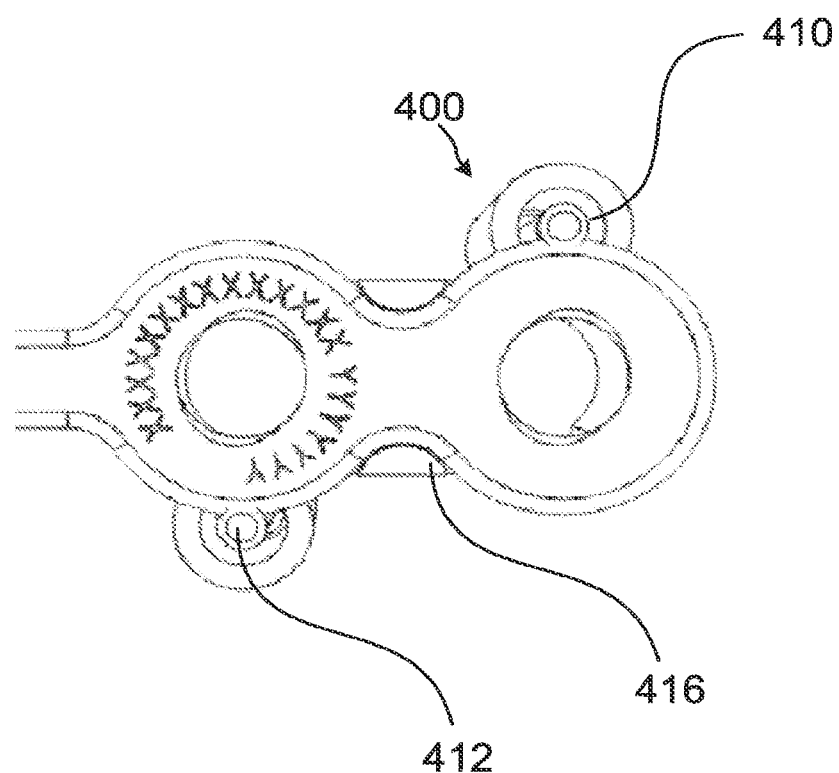
FIG. 21 illustrates a bottom view of the implant positioning device of FIG. 16 aligned with a plate in accordance with an embodiment of the disclosure.

Further, the second end has a retaining beam channel 414 formed around the retaining beam 412 to receive a side of the plate. The retaining beam channel 414 may be shaped to reflect a shape of the side of the plate to be received to removably couple the implant positioning device 400 to the plate, as shown in FIGS. 19-21.

According to one embodiment, the body 402 may have a substantially linear shape where the two fastener guides 403 form a line with each other. However, the body 402 may be shaped in a number of different ways to match a shape of a plate to be used.

The implant positioning device 400 may also include rails 416 that extend from the second/distal side of the body 402 between the two fastener guides 403 of the body 402. The rails 416 may couple to the plate and be used to prevent the plate from spinning and/or angular or rotational movement of the plate when removably coupled to the implant positioning device 400. Multiple rails 416 may be used to help position the plate in the proper orientation for attachment onto a bone or other body part. In addition, each rail 416 may also have a rail channel 417 to receive an edge of the plate to removably couple the implant positioning device 400 to the plate and further limit movement of the plate, as show in FIGS. 20-21.

The body 402 may also have a handle recess 418. The handle recess 418 is configured to receive and removably couple to a handle (such as handle 124 described above and shown in FIG. 8) to the implant positioning device 400. In addition, the handle recess 418 may help prevent rotation of the implant positioning device 400 when attached to the handle 124. As illustrated, the handle recess 418 may be positioned between the two fastener guides 403 on an exterior of the body 402. The handles recess 418 may also have a secondary recess (not shown) to provide an additional connection point for the handle. For example, the secondary recesses may provide a connection point that rigidly attaches the handle 124 to the body 402.

As described above with respect to implant positioning devices 100 and 300, the implant positioning device 400 may be disposable or reusable, and pre-loaded with fasteners. In one example, the implant positioning device 400 may be preloaded with a fastener by placing the fastener in the first end of the fastener guide 403. This may include pushing the fastener into the fastener guide 403 until a head of the fastener is gripped and held in place by the retaining arm 404. The implant positioning device 400 may then be coupled to a plate by pushing the retaining beams 412 of the implant positioning device 400 onto the plate. This may cause the retaining beams 408 to move or flex and snap onto the side the plate. It should be appreciated that the implant positioning device 400 may be coupled to the plate prior to the insertion of the fastener.

Once the implant positioning device 400 is coupled to the plate and the fastener is inserted into the fastener guide 403, the implant positioning device 400 may provide a type of handle or holding zone that can be gripped by a user or other instrument. This allows the plate to be positioned on a bone or other body part. Once positioned, the fastener can be driven through the fastener guide 403 and fastener aperture on the plate, and into the bone or other body part by a fastener driver to couple the plate to the bone or other body part. As the fastener is driven through the fastener guide 403, the retaining arm 404 moves or flexes away from the body 402 to allow the fastener to move through the fastener guide 403.

Figure 22:
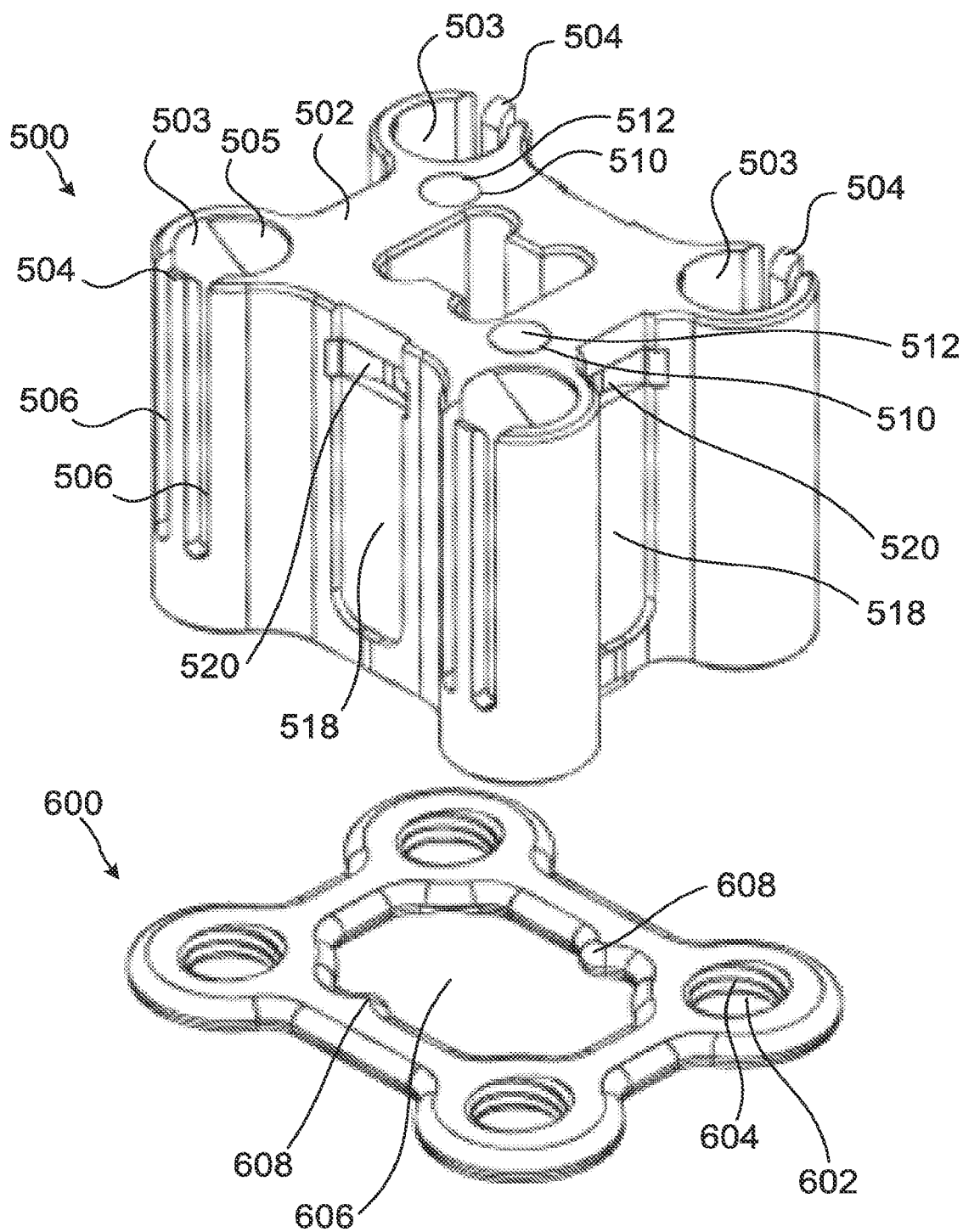
FIG. 22 illustrates a first perspective view of another implant positioning device in accordance with an embodiment of the disclosure.
Figure 23:
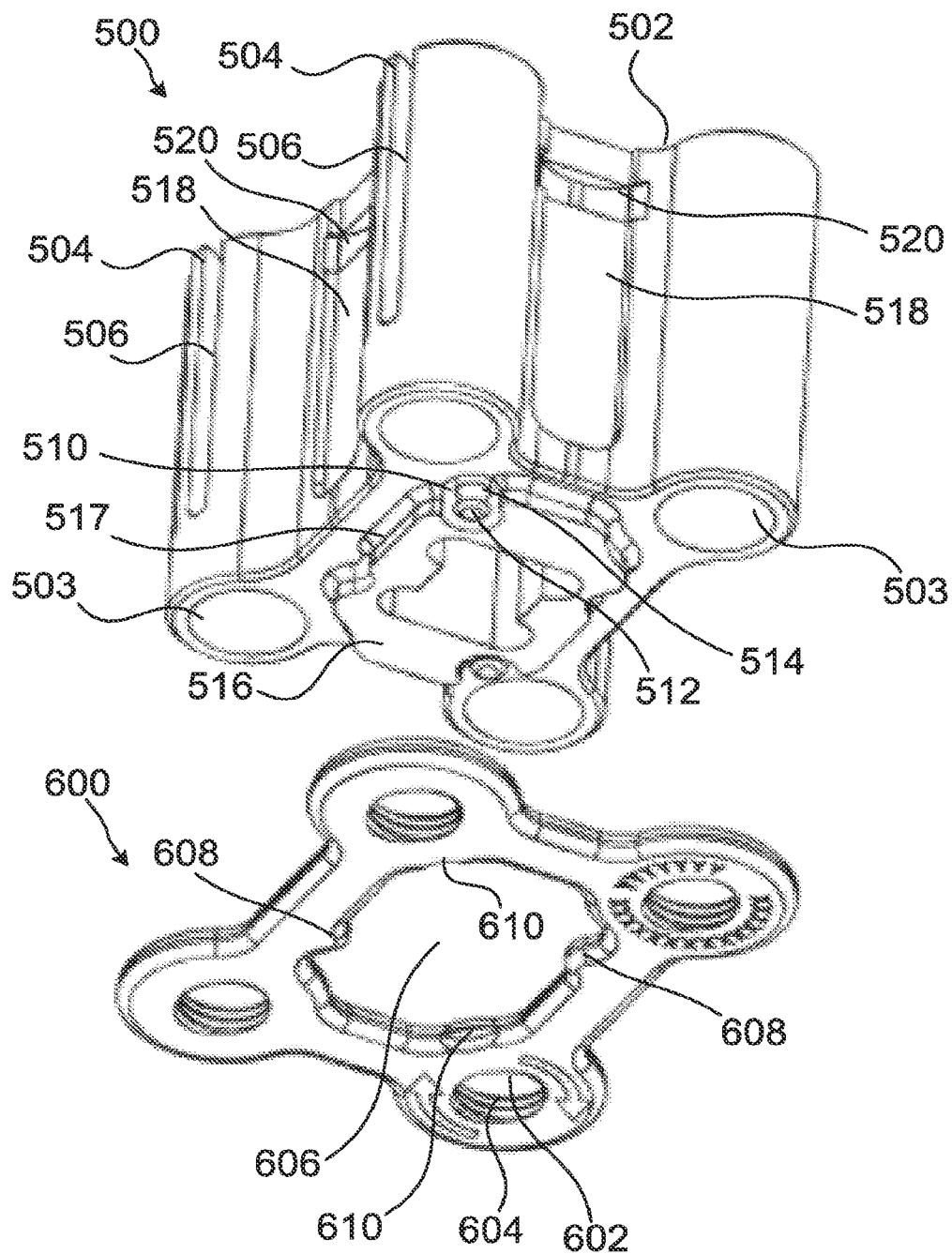
FIG. 23 illustrates a second perspective view of the implant positioning device of FIG. 22 in accordance with an embodiment of the disclosure.

FIGS. 22-23 illustrate another implant positioning device 500 for use with an implant fixation device according to an embodiment of the disclosure. As illustrated, the implant positioning device 500 includes a frame or a body 502 that has fastener guides 503. As described above with reference to the implant positioning device 100, each fastener guide 503 includes one or more retaining arms 504 (which may be firmer-like structures) formed on a first side or top side of the fastener guide 503 by slits or apertures 506. The retaining arms 504 are configured to releasably hold, guide, and position a fastener that may be used to couple an orthopaedic fixation device, such as a plate, to a bone or other body part. Each fastener guide 503 may also include an angled surface 505 formed inside the fastener guide 503 at the proximal or top end of the fastener guide 503. The angled surface 505 facilitates insertion and positioning of a fastener in the guide 503. The angled surface 505 may also form a lip at the proximal or top end of the fastener guide 503 that retains a fastener in the fastener guide 503 and reduces the risk of a fastener falling out of the fastener guide 503 if the positioning device 500 is tilted or turned upside down.

The top side of the implant positioning device 500 also allows a top of the fastener to be exposed. The fastener may be a screw, pin, rivet, and other type of fastener, etc., and the retaining arm 504 and slits 506 may serve as expansion zones to help capture a wide variety of fasteners effectively. As illustrated, the slits 506 are positioned on opposing sides of the retaining arms 504 and allow the retaining arms 504 to elastically move or flex to allow the fastener to be moved or pushed through the fastener guide 500, when the fastener is driven into a bone or other body part.

As illustrated, the implant positioning device 500 may include four fastener guides 503 oriented in a box type shape. However, the implant positioning device 500 may include more or less than four fastener guides 503 as needed. The retaining arm 504 may also be used to guide other instruments, for example, drills/drill hits, marking instruments to place markings, pegs, headless pins, etc. in a bone, which then serve as locating features to place plates or any other device before or after a resection is made, or after a fracture occurs.

The body 502 may include lumens, boreholes, channels or through-bores 510 at the first/top side of the implant positioning device 500 that extend to a second/bottom side, opposite for the first side. Each through-bore 510 is configured to receive a retaining beam 512, similar to one described above with reference to the implant positioning device 100 and shown in FIG. 5. Each retaining beam 512 may be inserted into the corresponding through-bore 510 and retained within the through-bore 510 by being press-fit within the through-bore 510. The retaining beam 512 may also be welded at the first/top side of the body 502 to ensure the retaining beam 512 remains within the through-bore 510. However, the retaining beam 512 may also be inserted into the through-bore 510 using a number of different methods. For example, the retaining beams 512 may be screwed into the through-bore 510 using threads that are formed on the top side of the retaining beam and through-bore.

The retaining beams 512, which are similar to retaining beams 112 described above and shown in FIG. 5, are configured to removably couple the implant positioning device 500 to a portion of a plate, such that the implant positioning device 500, or fastener disposed within the implant positioning device 500, is in alignment with a fastener aperture in the plate, for example, the plate 600 shown. While two retaining beams 512 are illustrated, the implant positioning device 500 may have additional or fewer retaining beams 512 as needed, to removably couple the fastener guide 500 with the plate.

Each retaining beam 512 has a first or top portion that is substantially the same size as a diameter of the through-bore 510 to ensure the retaining beam 512 can be press-fit into the through-bore 510. The retaining beam 512 also has a second or bottom portion that is opposite the first/top portion that has a diameter less than the diameter of the first portion. The second portion has a retaining beam channel 514 formed around the retaining beam 512 to receive a side of the plate. The retaining beam channel 514 may be shaped to reflect a shape of the side of the plate to be received to removably couple the implant positioning device 500 to the plate.

According to one embodiment, the body 502 may have a substantially square or box type shape. However, the body 502 may be shaped to in a number of different ways to match a shape of the plate to be used. The implant positioning device 500 may also include rails 516 that extend from the second/bottom side of the body 502. The rails 516 may be used to prevent a plate from spinning and/or angular or rotational movement of the plate when removably coupled to the implant positioning device 500. Multiple rails 516 or one rail 516 shaped to fit in an aperture of a plate, such as aperture 606 of plate 600, may be used to help position the plate in the proper orientation for attachment onto a bone or other body part. In addition, each rail 516 may also have a rail channel 517 to receive an edge of the plate to removably couple the plate to the implant positioning device 500 and further limit movement of the plate.

As described above with respect to the implant positioning device 100, the body 502 may also have a handle recess 518. The handle recess 518 is configured to receive and removably couple to a handle, for example, the handle 124 described above and shown in FIG. 8, to the implant positioning device 500. As illustrated, handle recesses 518 may be positioned between two adjacent fastener guides 503. The handles recesses 518 may also have secondary recesses 520 to provide an additional connection point for the handle. For example, the secondary recesses 520 may provide a connection point that rigidly attaches the handle 124 to the body 502.

The plate 600 includes one or more fastener apertures 602, each with grooves or threads 604 configured to receive a fastener to couple the plate 600 to a bone. The plate 600 includes an aperture 606 that is substantially in the middle of the plate 600. The aperture 606 may be configured to receive the rails 516 and retaining beams 512 of the implant positioning device 500 to removably couple the implant positioning, device 500 to the plate 600. For example, each retaining beam 512 may have a channel 514 and a side of the plate 600 may be configured to fit within the channel 514 disposed on a bottom end of the retaining beam 512 to removably couple the implant positioning device 500 to the plate 600. The plate 600 may also include protrusions 608 that extend from a middle portion of the plate 600. The protrusions may be keyed to the rails 516 and/or implant positioning device 500 and used to prevent the plate 600 from being coupled to the implant positioning device 500 in an incorrect orientation, i.e., upside down.

As described above with respect to the implant positioning device 100, the implant positioning device 500 may be preloaded with a fastener by placing the fastener in the first end of the fastener guide 503. This may include pushing the fastener into the fastener guide 503 until a head of the fastener is gripped and held in place by the retaining arm 504. The implant positioning device 500 may then be coupled to a plate, such as plate 600, by pushing the retaining beams 512 of the implant positioning device 500 onto the plate 600. This may cause the retaining beams 512 to move or flex towards each other, and then snap outwards away from each other onto the side of the plate 600, for example, into cutouts or recesses 610. The cutouts or recesses 610 may be keyed to receive the retaining beams 512 and couple the plate 600 to the implant positioning device 500. It should be appreciated that the implant positioning device 500 may be coupled to a plate, such as plate 600, prior to the insertion of the fastener.

As described above with respect to the implant positioning device 100, once the implant positioning device 500 is coupled to the plate 600 and the fastener is inserted into the fastener guide 503, the implant positioning device 500 may provide a type of handle or holding zone that can be gripped by a user or other instrument. This allows the plate 600 to be positioned on a bone or other body part. As illustrated, the retaining beams 512 couple to the inner profile of the plate 600 within the aperture 606, and an outer peripheral shape of the implant positioning device 500 is smaller than an outer peripheral shape of the plate 600. This allows the entire periphery of the plate 600 to be visible when the implant positioning device 500 is coupled to the plate 600.

Once the plate 600 is positioned, the fastener can be driven through the fastener guide 503 and fastener aperture 602, and into the bone or other body part by a fastener driver to couple the plate 600 to the bone or other body part. As the fastener is driven through the fastener guide 503, the retaining arm 504 moves or flexes away from the body 502 to allow the fastener to move through the fastener guide 503.

Figure 24:
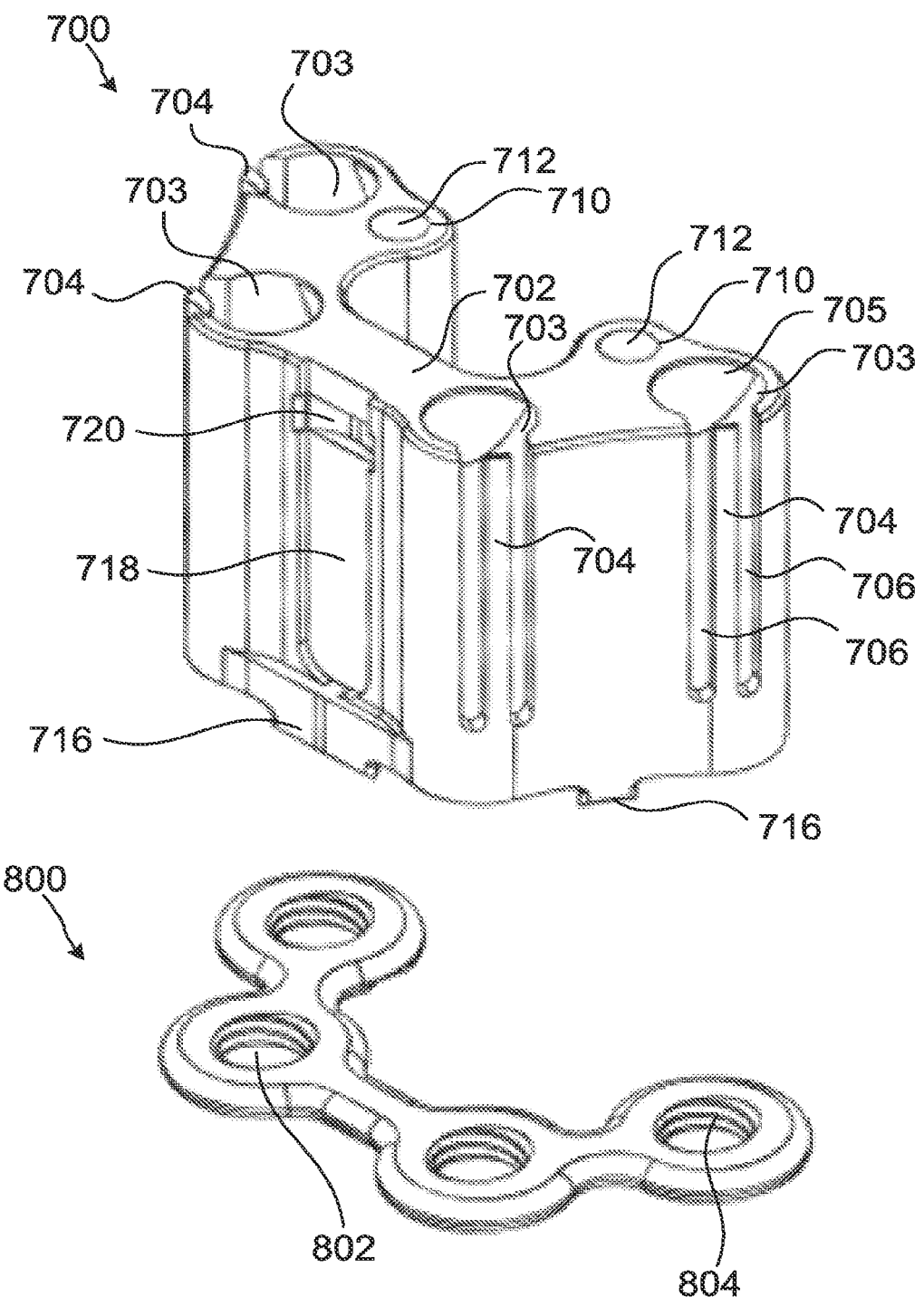
FIG. 24 illustrates a first perspective view of another implant positioning device in accordance with an embodiment of the disclosure.
Figure 25:
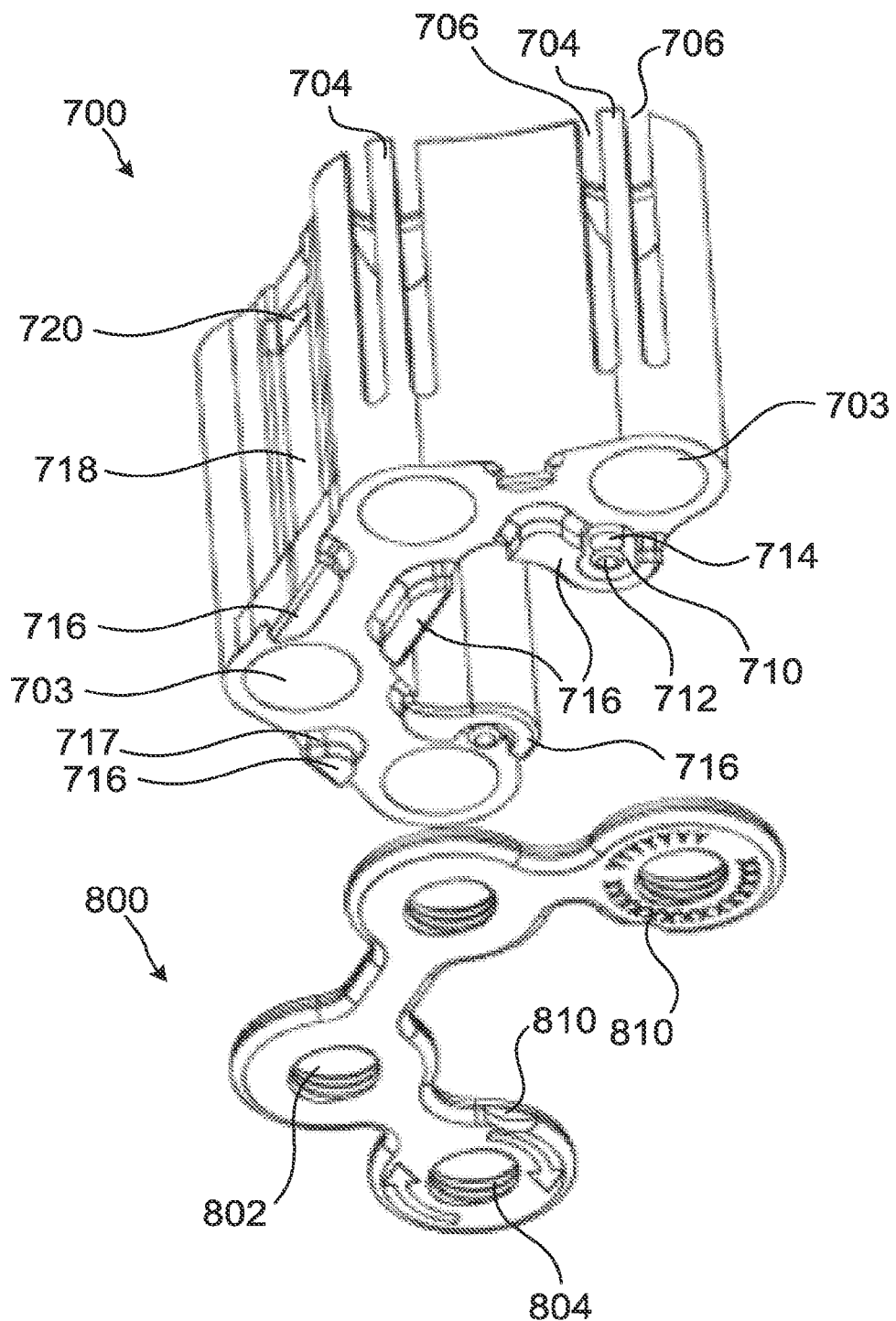
FIG. 25 illustrates a second perspective view of the implant positioning device of FIG. 24 in accordance with an embodiment of the disclosure.

FIGS. 24-25 illustrate another implant positioning device 700 for use with an implant fixation device according to an embodiment of the disclosure. As illustrated, the implant positioning device 700 includes a frame or a body 702 that has fastener guides 703. As described above with reference to the implant positioning device 100, each fastener guide 703 includes one or more retaining arms 704 (which may be finger-like structures) formed on a first side or top side of the fastener guide 703 by slits or apertures 706. The retaining arms 704 are configured to releasably hold, guide, and position a fastener that may be used to couple an orthopaedic fixation device, such as a plate, to a bone or other body part. Each fastener guide 703 may also include an angled surface 705 formed inside the fastener guide 703 at the proximal or top end of the fastener guide 703. The angled surface 705 facilitates insertion and positioning of a fastener in the guide 703. The angled surface 705 may also form a lip at the proximal or top end of the fastener guide 703 that retains a fastener in the fastener guide 703 and reduces the risk of a fastener falling out of the fastener guide 703 if the positioning device 700 is tilted or turned upside down.

The top side of the implant positioning device 700 also allows a top of the fastener to be exposed. The fastener may be a screw, pin, rivet, and other type of fastener, etc., and the retaining arm 704 and slits 706 may serve as expansion zones to help capture a wide variety of fasteners effectively. As illustrated, the slits 706 are positioned on opposing sides of the retaining arms 704 and allow the retaining arms 704 to elastically move or flex to allow the fastener to be moved or pushed through the fastener guide 700, when the fastener is driven into a bone or other body part.

As illustrated, the implant positioning device 700 may include four fastener guides 703 oriented in a V-type or U-type shape. However, the implant positioning device 700 may include more or less than four fastener guides 703 as needed. The retaining arm 704 may also be used to guide other instruments, for example, drills/drill bits, marking instruments to place markings, pegs, headless pins, etc. in a bone, which then serve as locating features to place plates or any other device before or after a resection is made, or after a fracture occurs.

The body 702 may include lumens, boreholes, channels or through-bores 710 at the first/top side of the implant positioning device 700 that extend to a second/bottom side, opposite for the first side. Each through-bore 710 is configured to receive a retaining beam 712, similar to one described above with reference to the implant positioning device 100 and shown in FIG. 5. Each retaining beam 712 may be inserted into the corresponding through-bore 710 and retained within the through-bore 710 by being press-fit within the through-bore 710. The retaining beam 712 may also be welded at the first/top side of the body 702 to ensure the retaining beam 712 remains within the through-bore 710. However, the retaining beam 712 may also be inserted into the through-bore 710 using a number of different methods. For example, the retaining beams 712 may be screwed into the through-bore 710 using threads that are formed on the top side of the retaining beam and through-bore.

The retaining beams 712, which are similar to retaining beams 112 described above and shown in FIG. 5, are configured to removably couple the implant positioning device 700 to a portion of a plate, such that the implant positioning device 700, or fastener disposed within the implant positioning device 700, is in alignment with a fastener aperture in the plate, for example, the plate 800 shown. While two retaining beam 712 are illustrated, the implant positioning device 700 may have additional or fewer retaining beams 712 as needed, to removably couple the fastener guide 700 with the plate.

Each retaining beam 712 has a first or top portion that is substantially the same size as a diameter of the through-bore 710 to ensure the retaining beam 712 can be press-fit into the through-bore 710. The retaining beam 712 also has a second or bottom portion that is opposite the first/top portion that has a diameter less than the diameter of the first portion. The second portion has a retaining beam channel 714 formed around the retaining beam 712 to receive a side of the plate. The retaining beam channel 714 may be shaped to reflect a shape of the side of the plate to be received to removably couple the implant positioning device 700 to the plate.

According to one embodiment, the body 702 may have a substantially V-type or U-type shape. However, the body 702 may be shaped to in a number of different ways to match a shape of the plate to be used. The implant positioning device 700 may also include rails 716 that extend from the second/bottom side of the body 702. The rails 716 may be used to prevent a plate from spinning and/or angular or rotational movement of the plate when removably coupled to the implant positioning device 700. Multiple rails 716 may be used to help position the plate in the proper orientation for attachment onto a bone or other body part. In addition, each rail 716 may also have a rail channel 717 to receive an edge of the plate to removably couple the plate to the implant positioning device 700 and further limit movement of the plate.

As described above with respect to the implant positioning device 100, the body 702 may also have a handle recess 718. The handle recess 718 is configured to receive and removably couple to a handle, for example, the handle 124 described above and shown in FIG. 8, to the implant positioning device 700. As illustrated, handle recesses 718 may be positioned between two adjacent fastener guides 703. The handles recesses 718 may also have secondary recesses 720 to provide an additional connection point for the handle. For example, the secondary recesses 720 may provide a connection point that rigidly attaches the handle 124 to the body 702.

The plate 800 includes one or more fastener apertures 802, each with grooves or threads 804 configured to receive a fastener to couple the plate 800 to a bone. The plate 800 is substantially V-shaped or U-shaped and may be configured to receive the rails 716 and retaining beams 712 of the implant positioning device 700 to removably couple the implant positioning device 700 to the plate 800. For example, each retaining beam 712 may have a channel 714 and a side of the plate 800 may be configured to fit within the channel 714 to removably couple the implant positioning device 700 to the plate 800.

As described above with respect to the implant positioning device 100, the implant positioning device 700 may be preloaded with a fastener by placing the fastener in the first end of the fastener guide 703. This may include pushing the fastener into the fastener guide 703 until a head of the fastener is gripped and held in place by the retaining arm 704. The implant positioning device 700 may then be coupled to a plate, such as plate 800, by pushing the retaining beams 712 onto the plate 800. This may cause the retaining beams 712 to move or flex towards each other, and then snap outwards away from each other onto the side of the plate 800, for example, into cutouts or recesses 810. The cutouts or recesses 810 may be keyed to receive the retaining beams 712 and couple the plate 800 to the implant positioning device 700. It should be appreciated that the implant positioning device 700 may be coupled to a plate, such as plate 800, prior to the insertion of the fastener.

As illustrated, the retaining beams 712 couple to the inner profile of the V-shape of plate 800, and an outer peripheral shape of the implant positioning device 700 is smaller than an outer peripheral shape of the plate 800. This allows the outer periphery of the plate 800 to be visible when the implant positioning device 700 is coupled to the plate 800.

Figure 26:
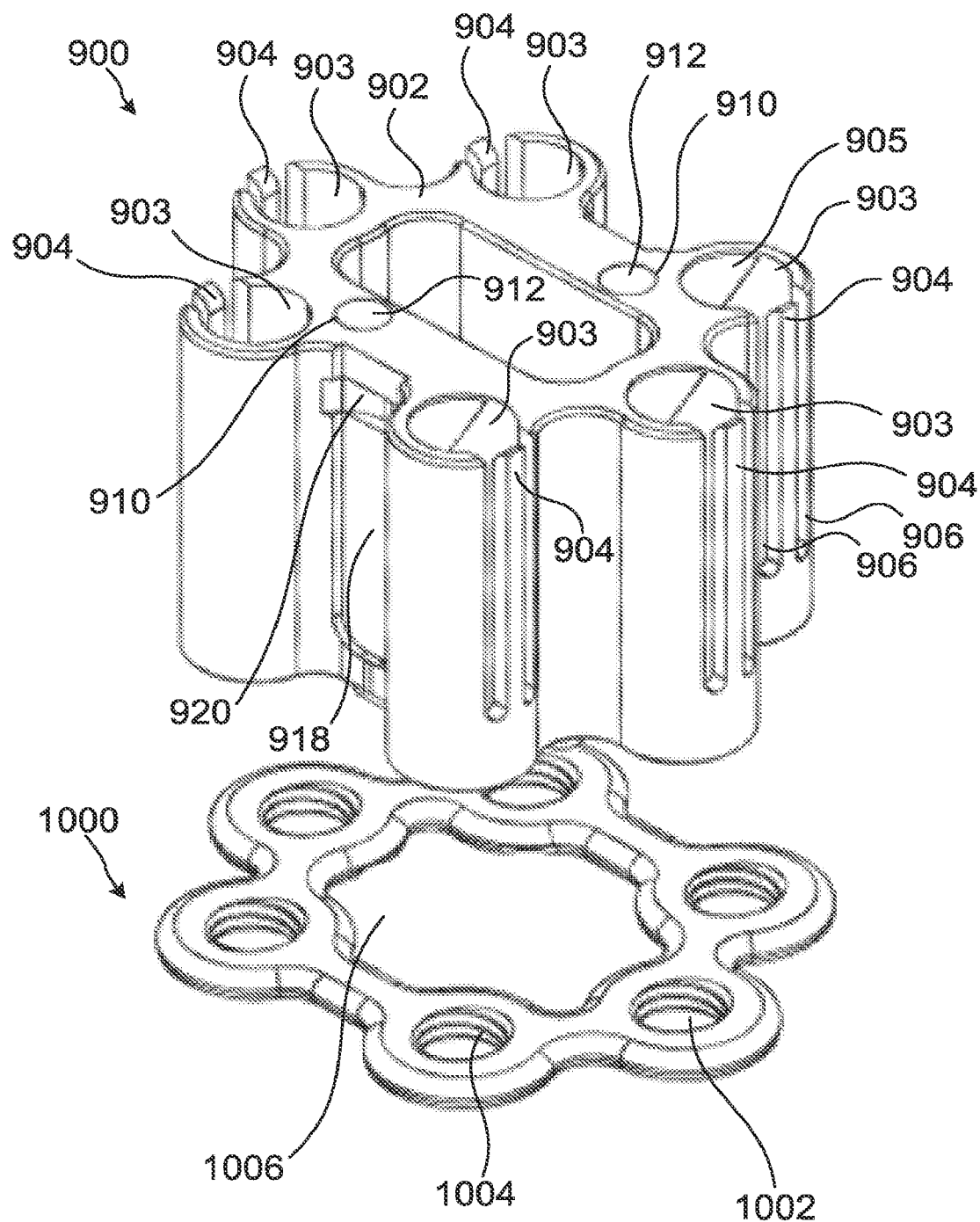
FIG. 26 illustrates a first perspective view of another implant positioning device in accordance with an embodiment of the disclosure.
Figure 27:
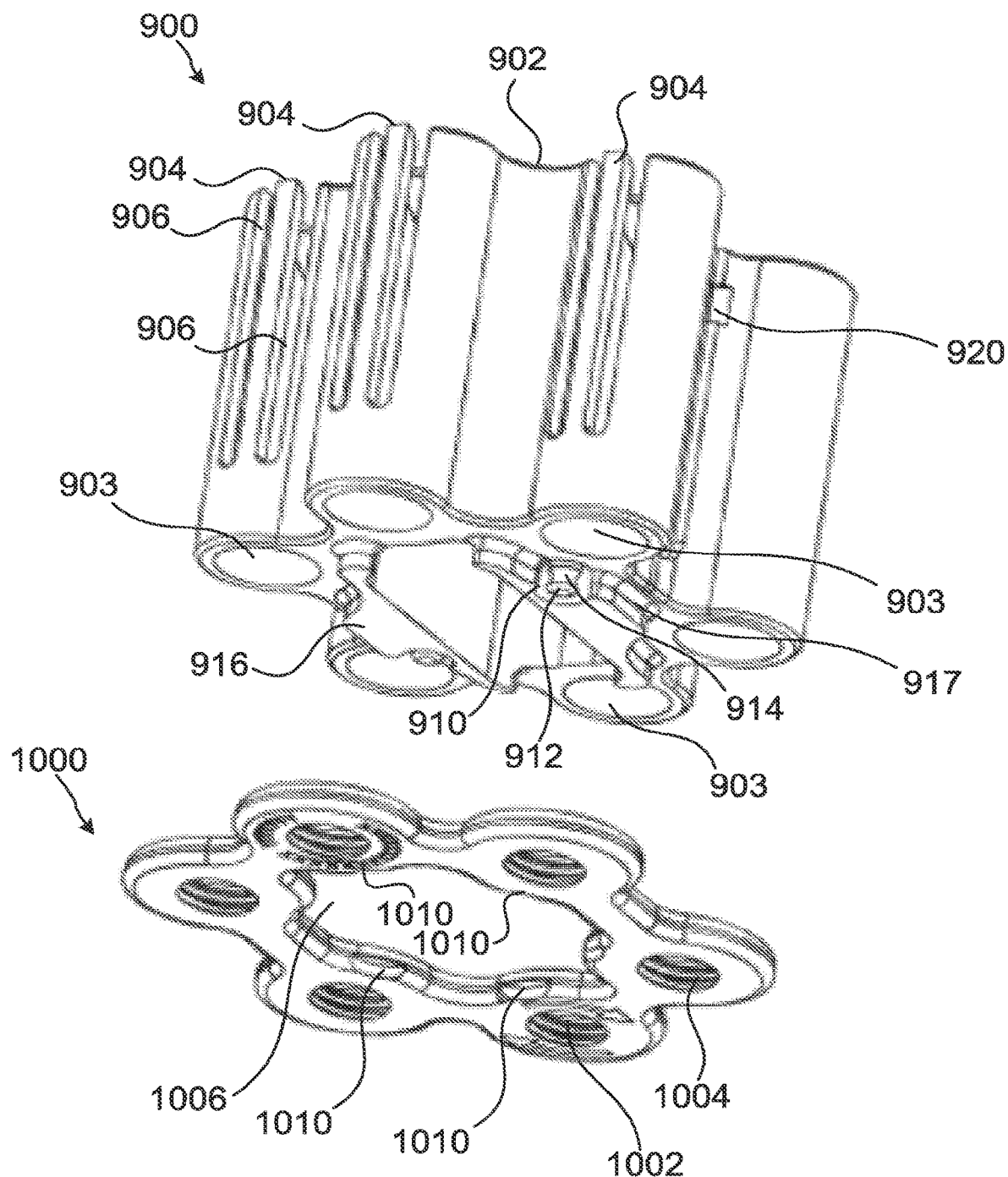
FIG. 27 illustrates a second perspective view of the implant positioning device of FIG. 26 in accordance with an embodiment of the disclosure.

FIGS. 26-27 illustrate another implant positioning device 900 for use with an implant fixation device according to an embodiment of the disclosure. As illustrated, the implant positioning device 900 includes a frame or a body 902 that has fastener guides 903. As described above with reference to the implant positioning device 100, each fastener guide 903 includes one or more retaining arms 904 (which may be finger-like structures) formed on a first side or top side of the fastener guide 903 by slits or apertures 906. The retaining arms 904 are configured to releasably hold, guide, and position a fastener that may be used to couple an orthopaedic fixation device, such as a plate, to a bone or other body part. Each fastener guide 903 may also include an angled surface 905 formed inside the fastener guide 903 at the proximal or top end of the fastener guide 903. The angled surface 905 facilitates insertion and positioning of a fastener in the guide 903. The angled surface 905 may also form a lip at the proximal or top end of the fastener guide 903 that retains a fastener in the fastener guide 903 and reduces the risk of a fastener falling out of the fastener guide 903 if the positioning device 900 is tilted or turned upside down.

The top side of the implant positioning device 900 also allows a top of the fastener to be exposed. The fastener may be a screw, pin, rivet, and other type of fastener, etc., and the retaining arm 904 and slits 906 may serve as expansion zones to help capture a wide variety of fasteners effectively. As illustrated, the slits 906 are positioned on opposing sides of the retaining aims 904 and allow the retaining aims 904 to elastically move or flex to allow the fastener to be moved or pushed through the fastener guide 900, when the fastener is driven into a bone or other body part.

As illustrated, the implant positioning device 900 may include six fastener guides 903 oriented in a circular type or O-type shape. However, the implant positioning device 900 may include more or less than six fastener guides 903 as needed. The retaining arm 904 may also be used to guide other instruments, for example, drills/drill bits, marking instruments to place markings, pegs, headless pins, etc. in a bone, which then serve as locating features to place plates or any other device before or after a resection is made, or after a fracture occurs.

The body 902 may include lumens, boreholes, channels or through-bores 910 at the first/top side of the implant positioning device 900 that extend to a second/bottom side, opposite for the first side. Each through-bore 910 is configured to receive a retaining beam 912, similar to one described above with reference to the implant positioning device 100 and shown in FIG. 5. Each retaining beam 912 may be inserted into the corresponding through-bore 910 and retained within the through-bore 910 by being press-fit within the through-bore 910. The retaining beam 912 may also be welded at the first/top side of the body 902 to ensure the retaining beam 912 remains within the through-bore 910. However, the retaining beam 912 may also be inserted into the through-bore 910 using a number of different methods. For example, the retaining beams 912 may be screwed into the through-bore 910 using threads that are formed on the top side of the retaining beam and through-bore.

The retaining beams 912, which are similar to retaining beams 112 described above and shown in FIG. 5, are configured to removably couple the implant positioning device 900 to a portion of a plate, such that the implant positioning device 900, or fastener disposed within the implant positioning device 900, is in alignment with a fastener aperture in the plate, for example, the plate 1000 shown. While two retaining beam 912 are illustrated, the implant positioning device 900 may have additional or fewer retaining beams 912 as needed, to removably couple the fastener guide 900 with the plate.

Each retaining beam 912 has a first or top portion that is substantially the same size as a diameter of the through-bore 910 to ensure the retaining beam 912 can be press-fit into the through-bore 910. The retaining beam 912 also has a second or bottom portion that is opposite the first/top portion that has a diameter less than the diameter of the first portion. The second portion has a retaining beam channel 914 formed around the retaining beam 912 to receive a side of the plate. The retaining beam channel 914 may be shaped to reflect shape of the side of the plate to be received to removably couple the implant positioning device 900 to the plate.

According to one embodiment, the body 902 may have a substantially circular shape. However, the body 902 may be shaped in a number of different ways to match a shape of the plate to be used. The implant positioning device 900 may also include rails 916 that extend from the second/bottom side of the body 902. The rails 916 may be used to prevent a plate from spinning and/or angular or rotational movement of the plate when removably coupled to the implant positioning device 900. Multiple rails 916 or one rail 916 shaped to fit in an aperture of a plate, such as aperture 1006 of plate 1000, may be used to help position the plate in the proper orientation for attachment onto a bone or other body part. In addition, each rail 916 may also have a rail channel 917 to receive an edge of the plate to removably couple the plate to the implant positioning device 900 and further limit movement of the plate.

As described above with respect to the implant positioning device 100, the body 902 may also have a handle recess 918. The handle recess 918 is configured to receive and removably couple to a handle, for example, the handle 124 described above and shown in FIG. 8, to the implant positioning device 900. As illustrated, handle recess 918 may be positioned between two adjacent fastener guides 903. The handles recess 918 may also have a secondary recess 920 to provide an additional connection point for the handle. For example, the secondary recesses 920 may provide a connection point that rigidly attaches the handle 124 to the body 902.

The plate 1000 includes one or more fastener apertures 1002, each with grooves or threads 1004 configured to receive a fastener to couple the plate 1000 to a bone. The plate 1000 includes an aperture 1006 that is substantially in the middle of the plate 1000. The aperture 1006 may be configured to receive the rails 916 and retaining beams 912 of the implant positioning device 900 to removably couple the implant positioning device 900 to the plate 1000. For example, each retaining beam 912 may have a channel 914 and a side of the plate 1000 may be configured to fit within the channel 914 to removably couple the implant positioning device 900 to the plate 1000. The aperture 1006 may be keyed to the rails 916 and/or implant positioning device 900 and used to prevent the plate 1000 from being coupled to the implant positioning device 900 in an incorrect orientation.

As described above with respect to the implant positioning device 100, the implant positioning device 900 may be preloaded with a fastener by placing the fastener in the first end of the fastener guide 903. This may include pushing the fastener into the fastener guide 903 until a head of the fastener is gripped and held in place by the retaining arm 904. The implant positioning device 900 may then be coupled to a plate, such as plate 1000, by pushing the retaining beams 912 of the implant positioning device 900 onto the plate 1000. This may cause the retaining beams 912 to move or flex towards each other, and then snap outwards away from each other onto the side of the plate 1000, for example, into cutouts or recesses 1010. The cutouts or recesses 1010 may be keyed to receive the retaining beams 912 and couple the plate 1000 to the implant positioning device 900. It should be appreciated that, the implant positioning device 900 may be coupled to a plate, such as plate 1000, prior to the insertion of the fastener.

As illustrated, the retaining beams 912 couple to the inner profile of the plate 1000 within the aperture 1006, and an outer peripheral shape of the implant positioning device 900 is smaller than an outer peripheral shape of the plate 1000. This allows the periphery of the plate 1000 to be visible when the implant positioning device 900 is coupled to the plate 1000.

It should be appreciated that the plates described herein may have an anatomical concave or convex shape based on a contour of the shape of the bone or body part to which the plate is to be attached. Accordingly, an implant positioning device, such as the implant positioning devices described above, may have a contour that matches the contour of the plate to allow the implant positioning device to removably couple with the plate. In addition, the plates may be different shapes based on a shape of a plate needed to be used to reattach bones or other calcaneus body parts.

Figure 28:
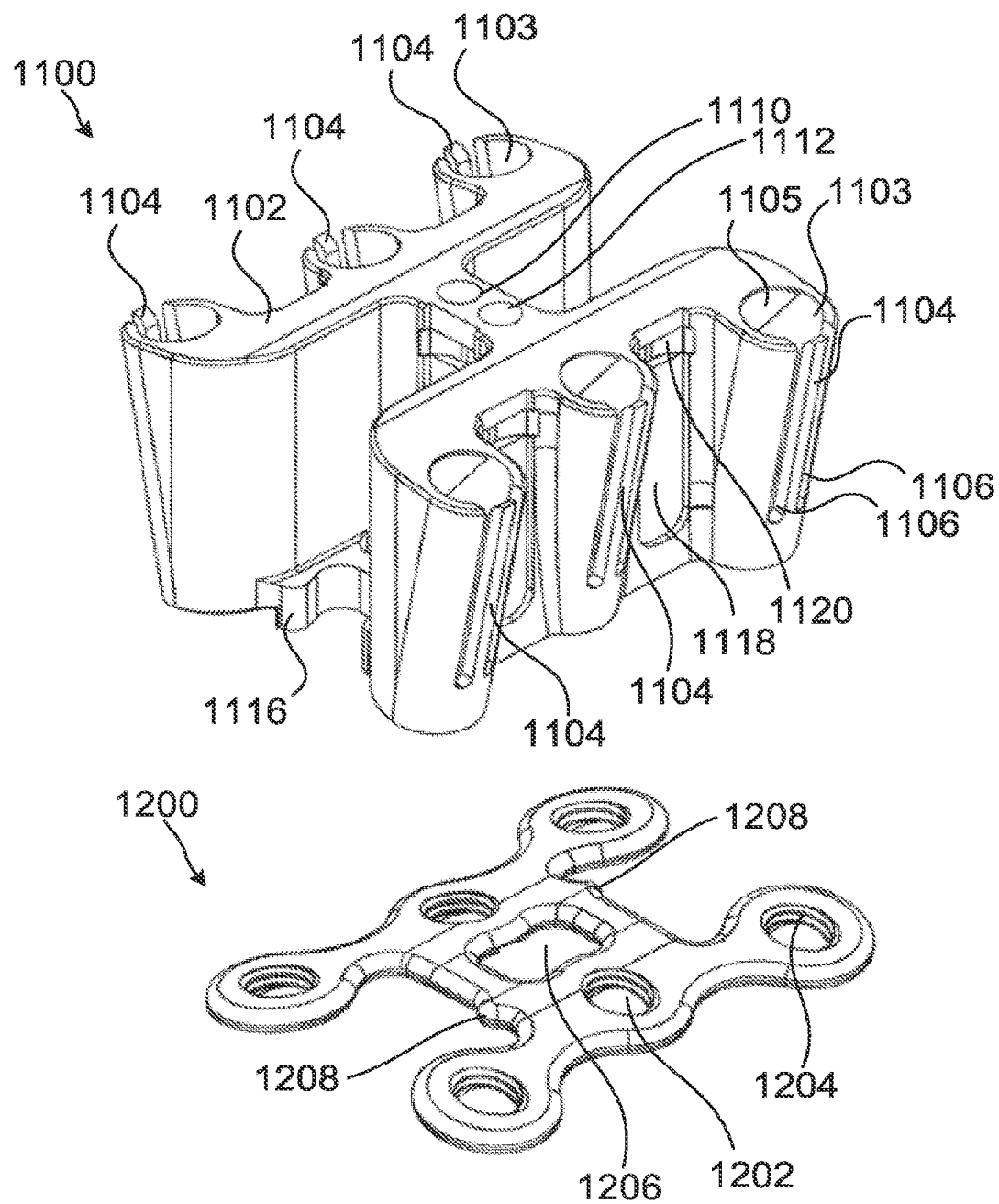
FIG. 28 illustrates a first perspective view of another implant positioning device in accordance with an embodiment of the disclosure.
Figure 29:
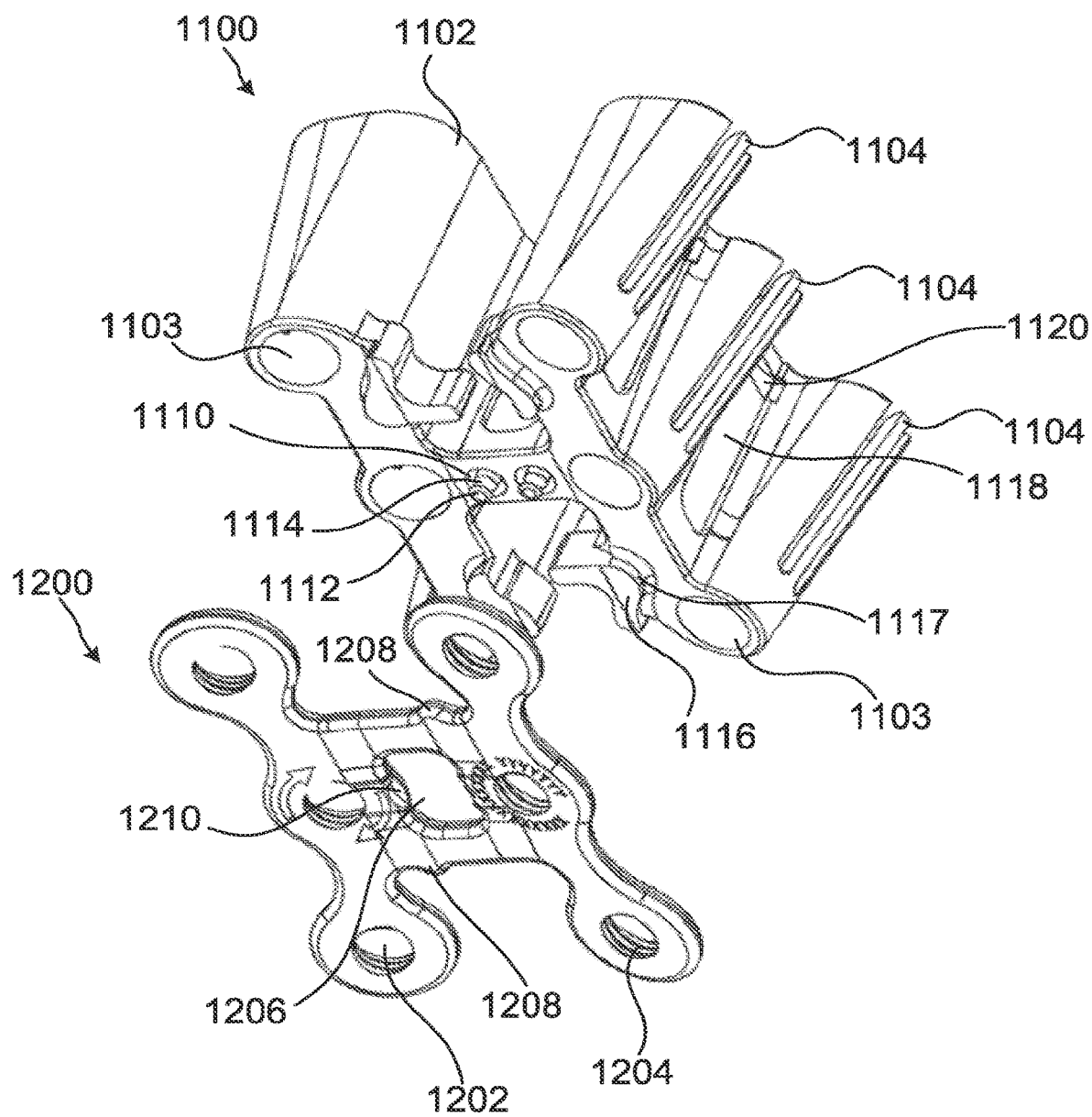
FIG. 29 illustrates a second perspective view of the implant positioning device of FIG. 28 in accordance with an embodiment of the disclosure.
Figure 30:
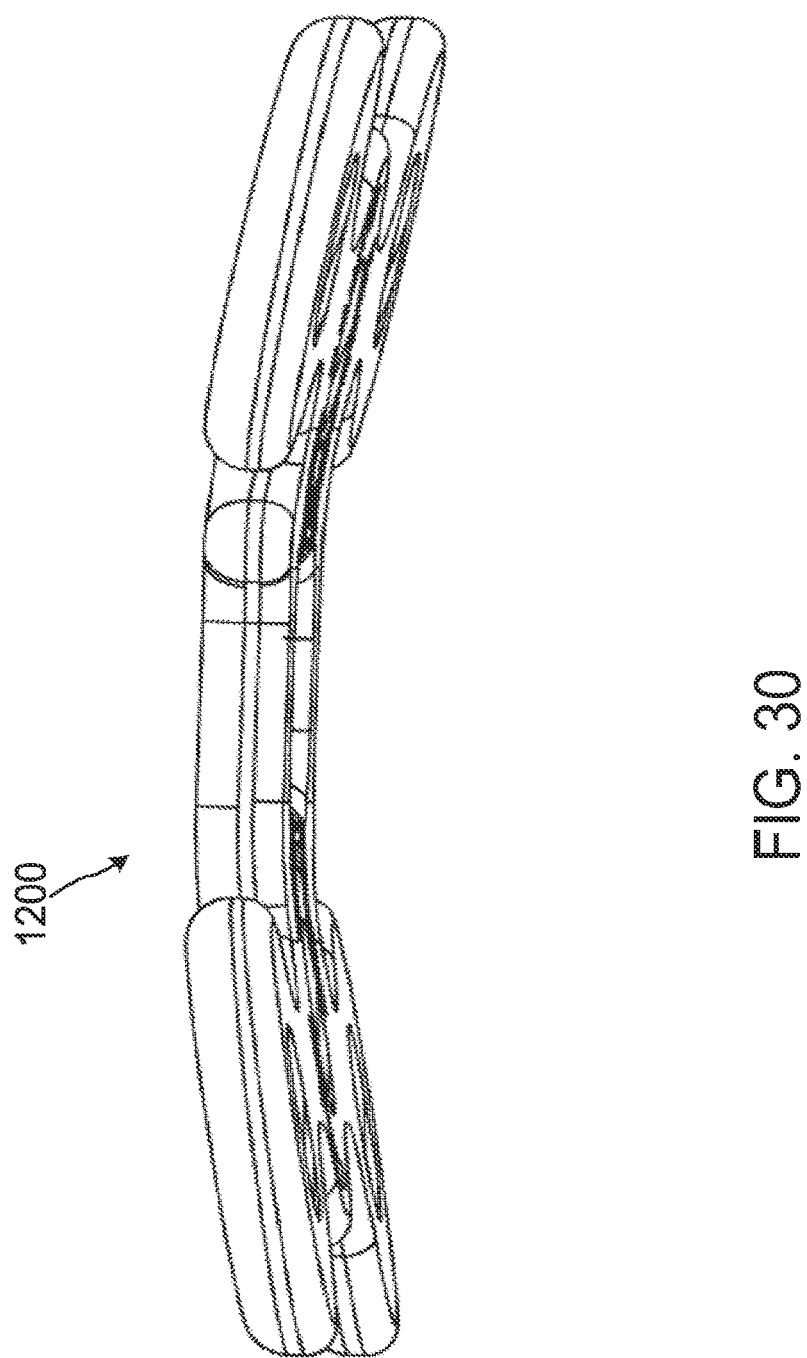
FIG. 30 illustrates a side view of a plate for use with the implant positioning device of FIG. 28 in accordance with an embodiment of the disclosure.

For example, FIGS. 28-30 illustrate an implant positioning device 1100 and plate 1200 that are contoured. The implant positioning device 1100 and plate 1200 are essentially the same as the implant positioning device 100 and plate 200 described above, and include the same features. For example, the implant positioning device 1100 includes a substantially H-shaped frame or a body 1102 with one or more fastener guides 1103. Each fastener guide 1103 includes one or more retaining arms 1104 (which may be finger-like structures) formed on a first end or proximal end of the fastener guide 1103 by slits or apertures 1106. Each fastener guide 1103 may also include an angled surface 1105 formed inside the fastener guide 1103 at the proximal or top end of the fastener guide 1103 that forms a lip and facilitates insertion and retention of a fastener in the guide 1103. The implant positioning device 1100 includes six fastener guides 1103. The body 1102 includes one or more lumens, boreholes, channels or through-bores 1110, and each through-bore 1110 is configured to receive a retaining beam 1112. Each retaining beam 1112 has a first or proximal portion and a second or distal portion that is opposite the first/proximal portion that has a diameter less than the diameter of the first portion. The second end has a retaining beam channel 1114 formed around the retaining beam 1112 to receive a side of a plate. The implant positioning device 1100 includes rails 1116 that extend from the second/distal side of the body 1102 proximal to an inner side of the legs of the H-shaped body 1102. Each rail 1116 may also have a rail channel 1117 adapted to receive an edge of the plate to removably couple the plate to the implant positioning device 1100 and further limit movement of the plate. The body 1102 also has one or more handle recesses 1118 configured to receive and removably couple a handle 124 (shown in FIG. 8) to the implant positioning device 1100. The handles recesses 1118 may also have secondary recesses 1120 to provide an additional connection point for the handle 124. For example, the secondary recesses 1120 may provide a connection point that rigidly attaches the handle 124 to the body 1102.

The difference between the implant positioning device 100 and the implant positioning device 1100 is that the implant positioning device 100 includes fastener guides 103 that are oriented to align with a flat plate, and the implant positioning device 1100 includes fastener guides 1103 that are oriented to align with a curved or contoured plate 1200.

Similarly, the plate 1200 includes one or more fastener apertures 1202, each with grooves or threads 1204 configured to receive a fastener to couple the plate 1200 to a bone. The plate 1200 includes an aperture 1206 that is substantially in the middle of the plate 1200. The plate 1200 may also include protrusions 1208 that extend from a middle portion of the plate 1200 to prevent the plate 1200 from being coupled to the implant positioning device 1100 in an incorrect orientation, i.e., upside down. When, the implant positioning device 1100 is coupled to the plate 1200, the retaining beams 1112 move or flex, and then snap onto the side of the plate 1200, for example, into cutouts or recesses 1210 formed in the plate 1200.

The difference between the plate 200 and the plate 1200 is that the plate 200 is substantially flat, and the plate 1200 is curved or contoured, for example to a shape of a bone or other body part to which the plate 1200 is to be attached.

For example, as illustrated in FIGS. 28-30, an axis extending perpendicular to the fastener apertures 1202 of plate 1200 is angled by about 1 degree to about 30 degrees with respect to an axis extending perpendicular to the aperture 1206. However, the fastener apertures 1202 may be disposed at any angle based on a contour of bone other body part to which the plate 1200 is to be attached.

In a similar manner, a longitudinal axis extending through to the fastener guides 1103 of implant positioning device 1100 is angled by about 1 degree to about 30 degrees with respect to a longitudinal axis of the retaining beams 1112 or through-borers 1110. However, the fastener guides 1103 may be disposed at any angle based on a contour of a plate to which the implant positioning device 1100 is to be coupled.

It should be appreciated that the plates described herein may have varying thicknesses, and a single plate may have more than one thickness based on a contour of the shape of the bone or body part to which the plate is to be attached. A plate may include one or more bridge portions (also referred to as a bridge plate) that provide clearance over a circumferential fixation modality (such as circumferential plates, wires, etc.). This allows a user to incorporate the benefits of using a plate (such as the plates described herein) along with circumferential techniques. Accordingly, an implant positioning device, such as the implant positioning devices described above, may be adapted to match the contour of the bridge plate to allow the implant positioning device to removably couple with the bridge plate.

Figure 31:
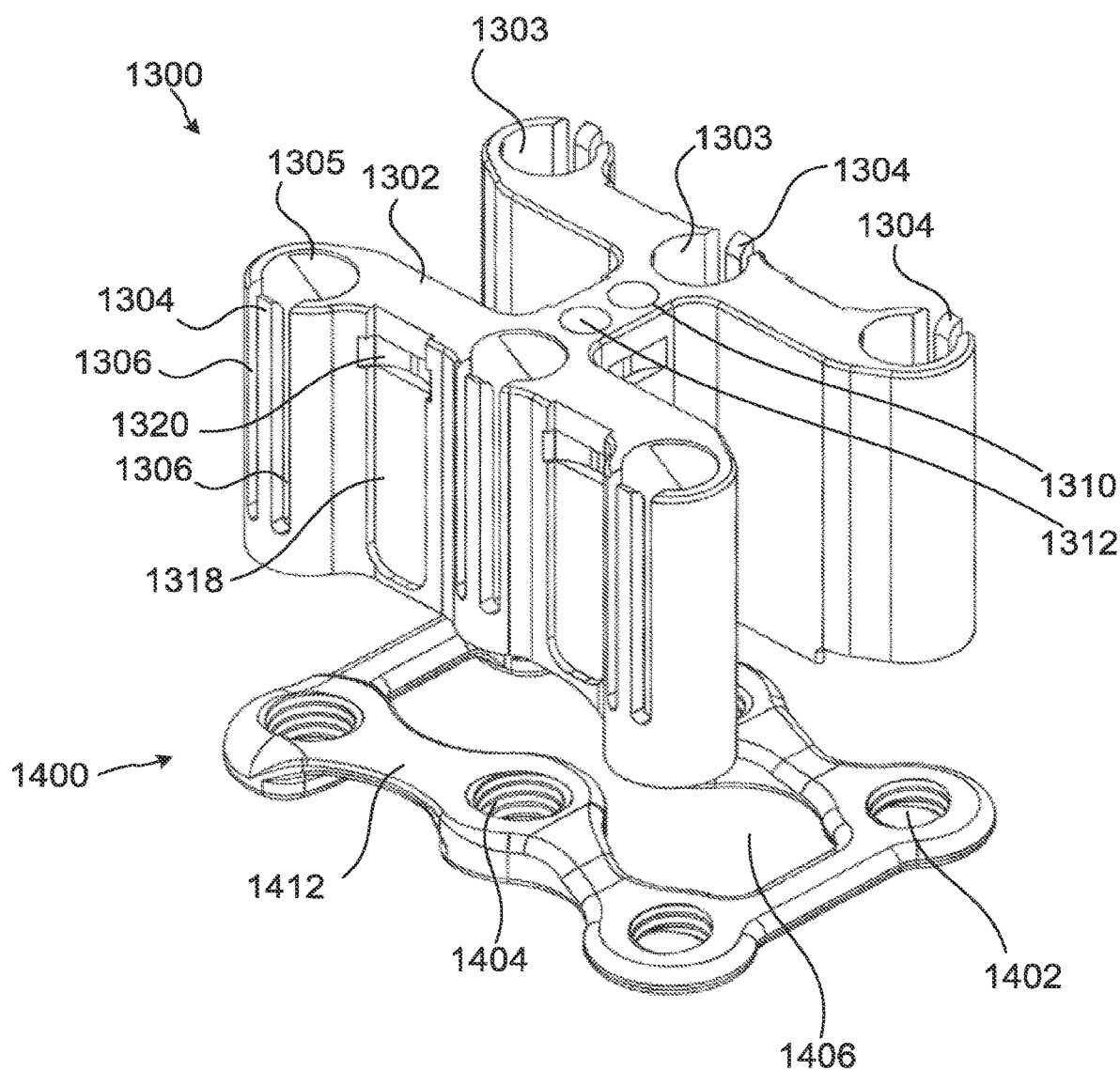
FIG. 31 illustrates a first perspective view of another implant positioning device in accordance with an embodiment of the disclosure.
Figure 32:
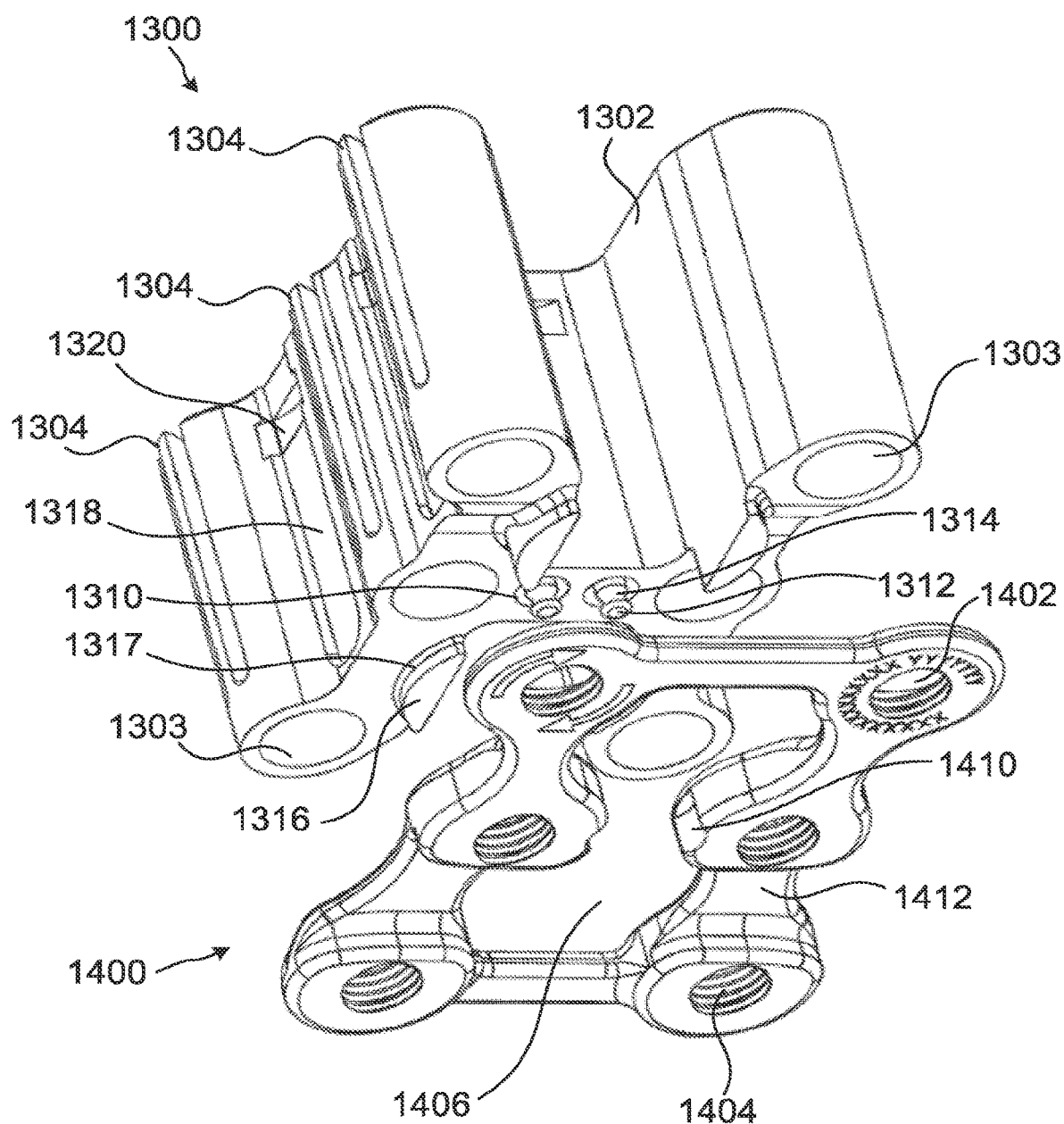
FIG. 32 illustrates a second perspective view of the implant positioning device of FIG. 31 in accordance with an embodiment of the disclosure.
Figure 33:
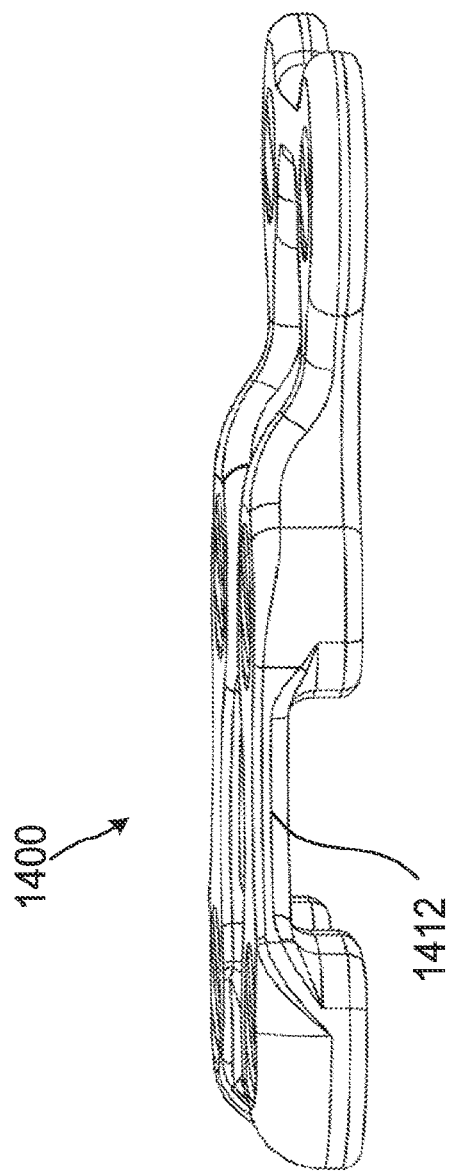
FIG. 33 illustrates a side view of a plate for use with the implant positioning device of FIG. 31 in accordance with an embodiment of the disclosure.

For example, FIGS. 31-33 illustrate an implant positioning device 1300 and a plate 1400 that is adapted to bridge a circumferential fixation modality (such as a circumferential plate, wire, etc.) coupled to a bone or other body part. The implant positioning device 1300 and plate 1400 are essentially the same as the implant positioning device 100 and plate 200 described above, and include the same features. For example, the implant positioning device 1300 includes a substantially H-shaped frame or a body 1302 with one or more fastener guides 1303. Each fastener guide 1303 includes one or more retaining arms 1304 (which may be finger-like structures) formed on a first end or proximal end of the fastener guide 1303 by slits or apertures 1306. Each fastener guide 1303 may also include an angled surface 1305 formed inside the fastener guide 1303 at the proximal or top end of the fastener guide 1303 that forms a lip and facilitates insertion and retention of a fastener in the guide 1303. The implant positioning device 1300 includes six fastener guides 1303. The body 1302 includes one or more lumens, boreholes, channels or through-bores 1310, and each through-bore 1310 is configured to receive a retaining beam 1312. Each retaining beam 1312 has a first or proximal portion and a second or distal portion that is opposite the first/proximal portion that has a diameter less than the diameter of the first portion. The second end has a retaining beam channel 1314 formed around the retaining beam 1312 to receive a side of a plate. The implant positioning device 1300 includes rails 1316 that extend from the second/distal side of the body 1302 proximal to an inner side of the legs of the H-shaped body 1302. Each rail 1316 may also have a rail channel 1317 adapted to receive an edge of the plate to removably couple the plate to the implant positioning device 1300 and further limit movement of the plate. The body 1302 also has one or more handle, recesses 1318 configured to receive and removably couple a handle 124 (shown in FIG. 8) to the implant positioning device 1300. The handles recesses 1318 may also have secondary recesses 1320 to provide an additional connection point for the handle 124. For example, the secondary recesses 1320 may provide a connection point that rigidly attaches the handle 124 to the body 1302.

The difference between the implant positioning device 100 and the implant positioning device 1300 is that the implant positioning device 100 includes fastener guides 103 that all have a same length, and the implant positioning device 1300 includes fastener guides 1303 that have differing lengths to couple to a bridge plate, such as plate 1400.

Similarly, the plate 1400 includes one or more fastener apertures 1402, each with grooves or threads 1404 configured to receive a fastener to couple the plate 1400 to a bone. The plate 1400 includes an aperture 1406 that is substantially in the middle of the plate 1400. When, the implant positioning device 1300 is coupled to the plate 1400, the retaining beams 1312 move or flex, and then snap onto the side of the plate 1400, for example, into cutouts or recesses 1410 formed in the plate 1400.

The difference between the plate 200 and the plate 1400 is that the plate 200 is substantially flat, and the plate 1400 includes a bridge section 1412. For example, as illustrated in FIGS. 31-33, the plate 1400 includes the bridge section 1412 that is adapted to provide a gap or space to accommodate a circumferential fixation modality (such as a circumferential plate, wire, etc.) coupled to a bone or other body part prior to the plate 1400, without interfering with the circumferential fixation modality. This causes the plate 1400 to have the bridge section 1412 and a varying thickness.

To accommodate the varying thickness and bridge section 1412, the fastener guides 1303 of implant positioning device 1300 have lengths that allow the implant positioning device 1300 to couple to the plate 1400. For example, two of the fastener guides 1303 of implant positioning device 1300 proximal to a bottom (or top depending on orientation) of the legs of the "H" have a length greater than a length of the other fastener guides 1303. Said another way, four of the fastener guides 1303 have a shorter length than a length of two of the fastener guides 1303 proximal to a bottom (or top depending on orientation) of the legs of the "H", in order to accommodate the raised bridge portion 1412 of the plate 1400.

Figure 34:
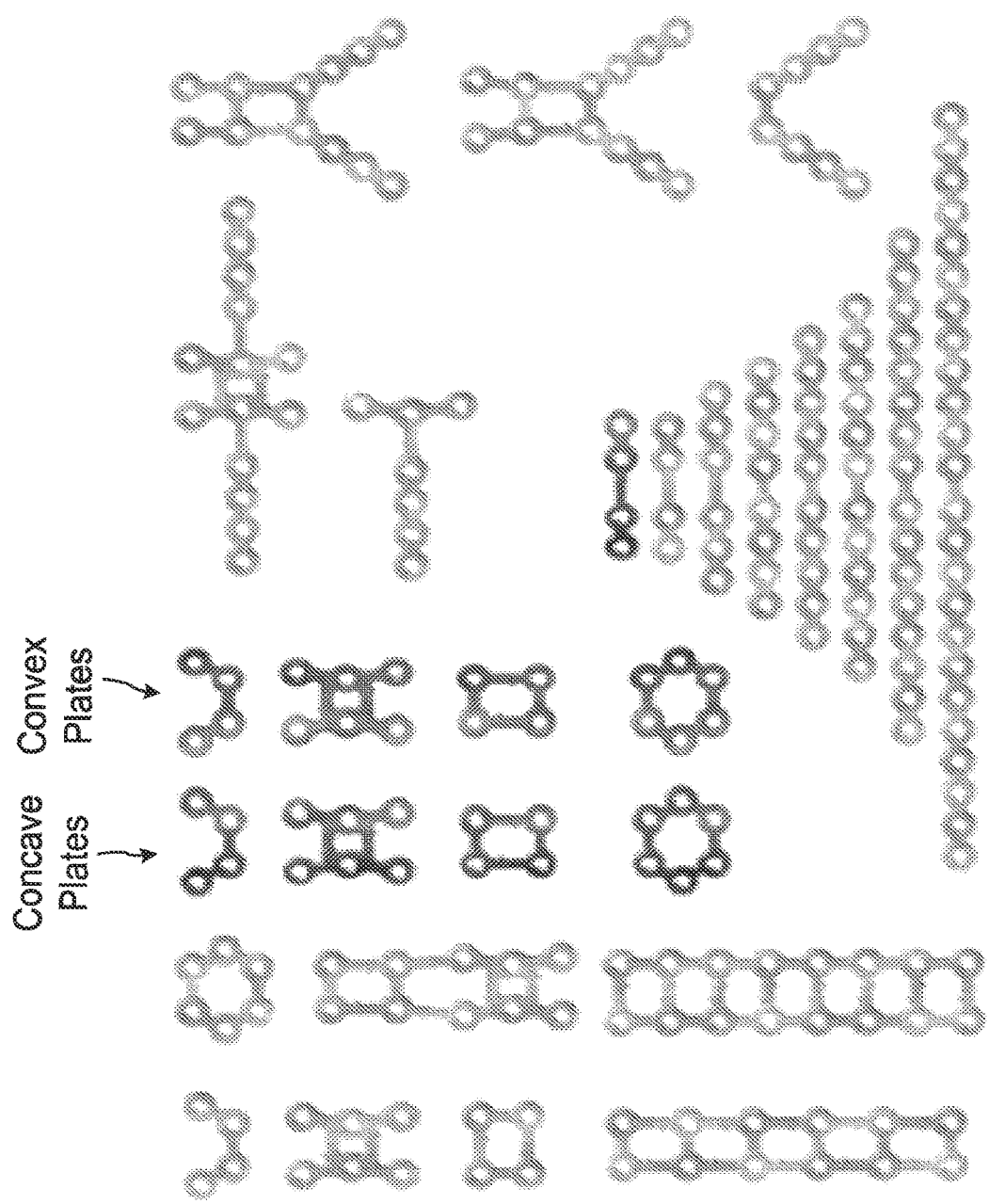
FIG. 34 illustrates various plates for use with implant positioners in accordance with embodiments of the disclosure.

It should be appreciated that the plates described herein may have any geometric shape, number of fastener apertures, be concave or convex, etc. based on a size and shape of the bone or body part to which the plate is to be attached. For example, FIG. 34 illustrates a non-exhaustive example of a number of various plates that can be used. It should be appreciated that any of the plates described herein may be modified or adapted to be bridge plates and/or contoured plates, and the corresponding implant positioners may be appropriately modified or adapted to accommodate the appropriate plate.

It should also be appreciated that one or more of the various features of each of the implant positioning devices described herein may be removed or incorporated into one another. For example, an outer peripheral shape of each implant positioning device may be smaller than an outer peripheral shape of the corresponding plate to allow the entire periphery of the plate to be visible when the implant positioning device is coupled to the plate. Further, each of the implant positioning devices described herein may be disposable or reusable, and pre-loaded with fasteners. For example, the implant positioning devices may be made of a semi-elastic material such that the retaining arms and retaining beams are able to expand without substantial deformation, such as a metal, polymer, plastic, etc.

Although the devices, systems, and methods have been described and illustrated in connection with certain embodiments, many variations and modifications should be evident to those skilled in the art and may be made without departing from the spirit and scope of the disclosure. The disclosure is thus not to be limited to the precise details of methodology or construction set firth above as such variations and modification are intended to be included within the scope of the disclosure.

What is claimed is:

1. A plating system, comprising:
a plate adapted to be coupled to a bone or other body part and including at least a first fastener aperture therein, the first fastener aperture extending through the plate from a first side of the plate to a second side of the plate for receiving a first fastener therethrough, the plate further including a plate side edge; and
an implant positioning device that includes a body with at least a first fastener guide therein, the implant positioning device snappable onto the plate for removably coupling the implant positioning device to the plate with the first fastener guide in alignment with the first fastener aperture, the implant positioning device including a first coupling member that extends from a bottom side of the body for engaging the plate side edge when the implant positioning device is snapped onto the plate, the first coupling member comprising a first rail that is immovable relative to the bottom side of the body, the implant positioning device further including a second coupling member that extends from the bottom side of the body for engaging the plate side edge when the implant positioning device is snapped onto the plate, the second coupling member being movable relative to the bottom side of the body,
wherein the second coupling member protrudes from an opening in the bottom side of the body.

2. The plating system of claim 1, wherein the body includes a first through-bore extending through the body along a first longitudinal axis from a top side of the body to the opening in the bottom side of the body, wherein the second coupling member is a distal portion of a retaining beam that is received in the first through-bore, wherein the implant positioning device has only a single retaining beam disposed in the first through-bore which is said retaining beam.

3. The plating system of claim 2, wherein, when snapping the implant positioning device onto the plate, the entirety of the second coupling member moves in a uniform direction relative to the first longitudinal axis of the first through-bore.

4. The plating system of claim 1, wherein the second coupling member is elastically deflectable relative to the bottom side of the body.

5. The plating system of claim 1, wherein, when snapping the implant positioning device onto the plate, the entirety of the second coupling member moves in a uniform direction relative to the bottom side of the body.

6. A plating system, comprising:
a plate adapted to be coupled to a bone or other body part and including at least a first fastener aperture therein, the first fastener aperture extending through the plate from a first side of the plate to a second side of the plate for receiving a first fastener therethrough, the plate further including a plate side edge; and
an implant positioning device that includes a body with at least a first fastener guide therein, the implant positioning device snappable onto the plate for removably coupling the implant positioning device to the plate with the first fastener guide in alignment with the first fastener aperture, the implant positioning device including a first coupling member that extends from a bottom side of the body for engaging the plate side edge when the implant positioning device is snapped onto the plate, the first coupling member comprising a first rail that is immovable relative to the bottom side of the body, the implant positioning device further including a second coupling member that extends from the bottom side of the body for engaging the plate side cadge when the implant positioning device is snapped onto the plate, the second coupling member being movable relative to the bottom side of the body, wherein the second coupling member comprises a second channel that is shaped to receive the plate side edge therein,
wherein the first rail is adjacent the second coupling member along the bottom side of the body and extends away from a first side of the second coupling member along the bottom side of the body, and wherein the first rail includes a first rail channel that is also shaped to receive the plate side edge therein such that, when the implant positioning device is snapped onto the plate, the plate side edge is received in the first rail channel and the second channel in succession along the plate side edge.

7. The plating system of claim 6, wherein the implant positioning device includes a second rail that extends from the bottom side of the body for engaging the plate side edge when the implant positioning device is snapped onto the plate, the second rail being immovable relative to the bottom side of the body.

8. The plating system of claim 6, wherein the implant positioning device includes a third coupling member that extends from the bottom side of the body for engaging the plate side edge when the implant positioning device is snapped onto the plate, the third coupling member being movable relative to the bottom side of the body.

9. The plating system of claim 6, wherein the second coupling member protrudes from an opening in the bottom side of the body.

10. A plating system, comprising:
a plate adapted to be coupled to a bone or other body part and including at least a first fastener aperture therein, the first fastener aperture extending through the plate from a first side of the plate to a second side of the plate for receiving a first fastener therethrough, the plate further including a plate side edge; and
an implant positioning device that includes a body with at least a first fastener guide therein, the implant positioning device snappable onto the plate for removably coupling the implant positioning device to the plate with the first fastener guide in alignment with the first fastener aperture, the implant positioning device including a first coupling member that extends from a bottom side of the body for engaging the plate side edge when the implant positioning device is snapped onto the plate, the first coupling member comprising a first rail that is immovable relative to the bottom side of the body, the implant positioning device further including a second coupling member that extends from the bottom side of the body for engaging the plate side edge when the implant positioning device is snapped onto the plate, the second coupling member bein movable relative to the bottom side of the body,
wherein the second coupling member is received in the first rail along the bottom side of the body.

11. The plating system of claim 10, wherein an outer peripheral shape of the body of the implant positioning device is smaller than an outer peripheral shape of the plate.

12. The plating system of claim 10, wherein the first rail includes a first rail portion situated on a first side of the second coupling member and a second rail portion situated on a second side of the second coupling member along the bottom side of the body.

13. The plating system of claim 10, wherein the implant positioning device includes a second rail that extends from the bottom side of the body for engaging the plate side edge when the implant positioning device is snapped onto the plate, the second rail being immovable relative to the bottom side of the body.

14. The plating system of claim 10, wherein the implant positioning device includes a third coupling member that extends from the bottom side of the body for engaging the plate side edge when the implant positioning device is snapped onto the plate, the third coupling member being movable relative to the bottom side of the body.

15. The plating system of claim 10, wherein the second coupling member protrudes from an opening in the bottom side of the body.

16. The plating system of claim 10, wherein the body includes a first through-bore extending through the body along a first longitudinal axis from a top side of the body to the bottom side of the body, wherein the second coupling member is a distal portion of a retaining beam that is received in the first through-bore, wherein the implant positioning device has only a single retaining beam disposed in the first through-bore which is said retaining beam.

17. A plating system, comprising:
a plate adapted to be coupled to a bone or other body, part and including at least a first fastener aperture therein the first fastener aperture extending through the plate from a first side of the plate to a second side of the plate for receiving a first fastener therethrough, the plate further including a plate side edge; and
an implant positioning device that includes a body with at least a first fastener guide therein, the implant positioning device snappable onto the plate for removably coupling the implant positioning device to the plate with the first fastener guide in alignment with the first fastener aperture, the implant positioning device including a first coupling member that extends from a bottom side of the body for engaging the plate side edge when the implant positioning device is snapped onto the plate, the first coupling member comprising a first rail that is immovable relative to the bottom side of the bod r, the implant positioning device further including a second coupling member that extends from the bottom side of the body for engagipg the plate side edge when the implant positioning device is snapped onto the plate, the second coupling member being movable relative to the bottom side of the body,
wherein the second coupling member is partially surrounded by the first rail along the bottom side of the body.

18. The plating system of claim 17, wherein the second coupling member extends through the first rail along the bottom side of the body.

19. The plating system of claim 17, wherein the implant positioning device includes a second rail that extends from the bottom side of the body for engaging the plate side edge when the implant positioning device is snapped onto the plate, the second rail being immovable relative to the bottom side of the body.

20. The plating system of claim 17, wherein the implant positioning device includes a third coupling member that extends from the bottom side of the body for engaging the plate side edge when the implant positioning device is snapped onto the plate, the third coupling member being movable relative to the bottom side of the body.

21. The plating system of claim 17, wherein the first rail includes a first rail portion situated on a first side of the second coupling member and a second rail portion situated on a second side of the second coupling member along the bottom side of the body.

* * * * *

UNITED STATES PATENT AND TRADEMARK OFFICE
CERTIFICATE OF CORRECTION

| | | |
|---|---|---|
| PATENT NO. | : 11,707,308 B2 | Page 1 of 1 |
| APPLICATION NO. | : 17/869563 | |
| DATED | : July 25, 2023 | |
| INVENTOR(S) | : Detweiler et al. | |

It is certified that error appears in the above-identified patent and that said Letters Patent is hereby corrected as shown below:

On the Title Page

On page 2, in Column 1, item [56], Line 2, delete "WO-201 9143690" and insert --WO-2019143690-- therefor In the Claims In Column 22, Line 10, in Claim 6, delete "cadge" and insert --edge-- therefor In Column 22, Line 13, in Claim 6, after "body,", insert a linebreak In Column 22, Line 64, in Claim 10, delete "bein" and insert --being-- therefor In Column 23, Line 33, in Claim 17, delete "body," and insert --body-- therefor In Column 23, Line 34, in Claim 17, delete "therein" and insert --therein,-- therefor In Column 24, Line 9, in Claim 17, delete "bod r," and insert --body,-- therefor In Column 24, Line 11, in Claim 17, delete "engagipg" and insert --engaging-- therefor Signed and Sealed this
Nineteenth Day of September, 2023

*Katherine Kelly Vidal*
Katherine Kelly Vidal
*Director of the United States Patent and Trademark Office*